(12) United States Patent
Malaviya et al.

(10) Patent No.: US 7,819,918 B2
(45) Date of Patent: Oct. 26, 2010

(54) IMPLANTABLE TISSUE REPAIR DEVICE

(75) Inventors: Prasanna Malaviya, Fort Wayne, IN (US); Herbert E. Schwartz, Fort Wayne, IN (US); Anthony D. Zannis, Fort Wayne, IN (US); Terrence David Whalen, Leesburg, IN (US); Philip Joseph Jenks, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 812 days.

(21) Appl. No.: 10/747,349

(22) Filed: Dec. 29, 2003

(65) Prior Publication Data

US 2004/0143344 A1 Jul. 22, 2004

Related U.S. Application Data

(63) Continuation-in-part of application No. 10/195,794, filed on Jul. 15, 2002.

(60) Provisional application No. 60/388,713, filed on Jun. 14, 2002, provisional application No. 60/305,786, filed on Jul. 16, 2001.

(51) Int. Cl.
*A61F 2/08* (2006.01)
(52) U.S. Cl. ............... 623/14.12; 623/8; 623/23.72; 623/23.63
(58) Field of Classification Search ............... 623/14.12, 623/23.72, 13.17, 23.52, 23.63, 8
See application file for complete search history.

(56) References Cited

U.S. PATENT DOCUMENTS

| | | | |
|---|---|---|---|
| 3,272,204 A * | 9/1966 | Artandi et al. ............... | 606/151 |
| 3,562,820 A | 2/1971 | Braun | |
| 3,867,728 A * | 2/1975 | Stubstad et al. .......... | 623/17.16 |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |

(Continued)

FOREIGN PATENT DOCUMENTS

EP 0446105 A2 1/1992

(Continued)

OTHER PUBLICATIONS

Hiles et al., "Mechanical properties of xenogeneic small-intestinal submucosa when used as an aortic graft in the dog", *Journal of Biomedical Materials Research*, vol. 29, 883-891, (1995).

(Continued)

*Primary Examiner*—Paul Prebilic

(57) ABSTRACT

An implantable tissue repair device has a cover and tissue regeneration material. The cover includes a top panel and a bottom panel joined together along a leading edge. The tissue regeneration material is positioned between the top and bottom panels. The cover includes a continuous sheet of biocompatible material extending across the edge and into the top panel and bottom panel. The cover is thicker along the leading edge than at least a portion of the top panel and thicker than at least a portion of the bottom panel. At least a portion of one of the panels covering the tissue regeneration material is thicker than a portion of the other panel covering the tissue regeneration material. A method of making the device is also disclosed.

19 Claims, 6 Drawing Sheets

U.S. PATENT DOCUMENTS

| | | |
|---|---|---|
| 4,190,040 A * | 2/1980 | Schulte .................... 128/899 |
| 4,205,399 A | 6/1980 | Shalaby et al. |
| 4,208,511 A | 6/1980 | Shalaby et al. |
| 4,349,921 A * | 9/1982 | Kuntz .................... 623/17.16 |
| 4,352,463 A * | 10/1982 | Baker ...................... 239/663 |
| 4,400,833 A | 8/1983 | Kurland |
| 4,418,691 A * | 12/1983 | Yannas et al. ............. 424/548 |
| 4,428,082 A * | 1/1984 | Naficy ........................ 623/8 |
| 4,610,397 A * | 9/1986 | Fischer et al. ............... 241/86 |
| 4,642,120 A | 2/1987 | Nevo et al. |
| 4,669,473 A | 6/1987 | Richards et al. |
| 4,703,108 A * | 10/1987 | Silver et al. ............... 530/356 |
| 4,705,040 A | 11/1987 | Mueller et al. |
| 4,741,330 A | 5/1988 | Hayhurst |
| 4,750,492 A | 6/1988 | Jacobs |
| 4,772,284 A * | 9/1988 | Jefferies et al. ................ 623/8 |
| 4,820,302 A * | 4/1989 | Woodroof ..................... 623/8 |
| 4,823,815 A * | 4/1989 | Watson et al. ............. 128/897 |
| 4,873,976 A | 10/1989 | Schreiber |
| 4,880,429 A * | 11/1989 | Stone .................... 623/14.12 |
| 4,902,508 A * | 2/1990 | Badylak et al. ............. 424/423 |
| 4,919,667 A | 4/1990 | Richmond |
| 4,956,178 A | 9/1990 | Badylak et al. |
| 4,956,179 A * | 9/1990 | Bamberg et al. ............ 424/114 |
| 4,976,715 A * | 12/1990 | Bays et al. .................... 606/77 |
| 5,007,934 A | 4/1991 | Stone |
| 5,061,286 A * | 10/1991 | Lyle ...................... 623/23.63 |
| 5,102,421 A * | 4/1992 | Anspach, Jr. ............... 606/232 |
| 5,108,438 A | 4/1992 | Stone |
| 5,128,326 A * | 7/1992 | Balazs et al. .................. 514/54 |
| RE34,021 E | 8/1992 | Mueller et al. |
| 5,171,280 A * | 12/1992 | Baumgartner ............. 623/17.12 |
| 5,197,882 A * | 3/1993 | Jernberg .................... 433/215 |
| 5,236,431 A * | 8/1993 | Gogolewski et al. .......... 606/72 |
| 5,236,454 A * | 8/1993 | Miller ........................... 623/8 |
| 5,246,441 A * | 9/1993 | Ross et al. ................... 606/53 |
| 5,258,015 A | 11/1993 | Li et al. |
| 5,269,809 A | 12/1993 | Hayhurst et al. |
| 5,275,826 A | 1/1994 | Badylak et al. |
| 5,281,422 A | 1/1994 | Badylak et al. |
| 5,306,307 A * | 4/1994 | Senter et al. ............. 623/17.16 |
| 5,306,311 A | 4/1994 | Stone et al. |
| 5,320,633 A | 6/1994 | Allen et al. |
| 5,329,846 A * | 7/1994 | Bonutti ....................... 100/50 |
| 5,350,583 A * | 9/1994 | Yoshizato et al. ......... 623/15.12 |
| 5,352,463 A * | 10/1994 | Badylak et al. ............. 424/551 |
| 5,368,051 A * | 11/1994 | Dunn et al. ................ 128/898 |
| 5,372,821 A | 12/1994 | Badylak et al. |
| 5,374,268 A | 12/1994 | Sander |
| 5,376,117 A * | 12/1994 | Pinchuk et al. ................. 623/8 |
| 5,376,118 A * | 12/1994 | Kaplan et al. ............. 623/23.72 |
| 5,380,334 A | 1/1995 | Torrier et al. |
| 5,445,833 A | 8/1995 | Badylak et al. |
| 5,447,940 A * | 9/1995 | Harvey et al. ............... 514/310 |
| 5,460,962 A | 10/1995 | Kemp |
| 5,464,929 A | 11/1995 | Bezwada et al. |
| 5,479,033 A | 12/1995 | Baca et al. |
| 5,514,181 A * | 5/1996 | Light et al. .............. 623/13.18 |
| 5,516,533 A | 5/1996 | Badylak et al. |
| 5,520,691 A | 5/1996 | Branch |
| 5,545,178 A | 8/1996 | Kensey et al. |
| 5,554,389 A | 9/1996 | Badylak et al. |
| 5,569,252 A | 10/1996 | Justin et al. |
| 5,571,189 A * | 11/1996 | Kuslich .................... 623/17.12 |
| 5,573,784 A | 11/1996 | Badylak et al. |
| 5,591,234 A * | 1/1997 | Kirsch ..................... 623/23.72 |
| 5,593,441 A * | 1/1997 | Lichtenstein et al. .......... 600/37 |
| 5,595,621 A * | 1/1997 | Light et al. .................. 156/80 |
| 5,595,751 A | 1/1997 | Bezwada et al. |
| 5,597,579 A | 1/1997 | Bezwada et al. |
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A | 6/1997 | Badylak et al. |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A * | 8/1997 | Saffran .................... 128/898 |
| 5,668,288 A | 9/1997 | Storey et al. |
| 5,669,912 A * | 9/1997 | Spetzler ..................... 606/72 |
| 5,677,355 A | 10/1997 | Shalaby et al. |
| 5,681,353 A | 10/1997 | Li et al. |
| 5,693,085 A * | 12/1997 | Buirge et al. .............. 623/1.13 |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,711,969 A | 1/1998 | Patel et al. |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A * | 4/1998 | Buirge ..................... 623/1.15 |
| 5,735,903 A | 4/1998 | Li et al. |
| 5,736,372 A * | 4/1998 | Vacanti et al. ............... 435/180 |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A * | 6/1998 | Valentini .................... 433/173 |
| 5,759,208 A * | 6/1998 | Zhen et al. ...................... 8/137 |
| 5,762,966 A | 6/1998 | Knapp et al. |
| 5,769,899 A | 6/1998 | Schwartz et al. |
| 5,773,577 A * | 6/1998 | Cappello .................. 530/350 |
| 5,788,625 A | 8/1998 | Plouhar et al. |
| 5,795,353 A * | 8/1998 | Felt ........................... 424/423 |
| 5,800,537 A * | 9/1998 | Bell ........................... 424/93.1 |
| 5,830,708 A * | 11/1998 | Naughton ................. 435/70.1 |
| 5,834,232 A * | 11/1998 | Bishop et al. ............... 435/68.1 |
| 5,842,477 A | 12/1998 | Naughton et al. |
| 5,847,012 A | 12/1998 | Shalaby et al. |
| 5,855,610 A | 1/1999 | Vacanti et al. |
| 5,855,613 A * | 1/1999 | Antanavich et al. ....... 623/23.72 |
| 5,855,619 A * | 1/1999 | Caplan et al. ............. 623/23.72 |
| 5,859,150 A | 1/1999 | Jamiolkowski et al. |
| 5,861,004 A | 1/1999 | Kensey et al. |
| 5,863,551 A * | 1/1999 | Woerly ....................... 424/423 |
| 5,866,414 A | 2/1999 | Badylak et al. |
| 5,885,619 A | 3/1999 | Patel et al. |
| 5,891,558 A | 4/1999 | Bell et al. |
| 5,899,939 A * | 5/1999 | Boyce et al. .............. 623/16.11 |
| 5,906,997 A | 5/1999 | Schwartz et al. |
| 5,916,265 A * | 6/1999 | Hu .............................. 424/423 |
| 5,922,024 A * | 7/1999 | Janzen et al. ................... 623/8 |
| 5,922,028 A | 7/1999 | Plouhar et al. |
| 5,939,323 A * | 8/1999 | Valentini et al. ............. 435/395 |
| 5,954,723 A * | 9/1999 | Spetzler ....................... 606/72 |
| 5,954,747 A | 9/1999 | Clark |
| 5,955,100 A | 9/1999 | Bosslet et al. |
| 5,958,874 A | 9/1999 | Clark et al. |
| 5,968,096 A | 10/1999 | Whitson et al. |
| 5,971,987 A | 10/1999 | Huxel et al. |
| 5,980,524 A | 11/1999 | Justin et al. |
| 5,981,802 A * | 11/1999 | Katz ........................... 564/468 |
| 5,981,825 A | 11/1999 | Brekke |
| 5,989,269 A | 11/1999 | Vibe-Hansen et al. |
| 5,989,280 A * | 11/1999 | Euteneuer et al. ............ 623/1.1 |
| 5,993,475 A | 11/1999 | Li et al. |
| 5,993,844 A | 11/1999 | Abraham et al. |
| 5,997,575 A | 12/1999 | Whitson et al. |
| 6,010,525 A | 1/2000 | Bonutti et al. |

| | | | |
|---|---|---|---|
| 6,017,301 A | 1/2000 | Schwartz et al. | |
| 6,017,348 A | 1/2000 | Hart et al. | |
| 6,027,744 A * | 2/2000 | Vacanti et al. | 424/426 |
| 6,034,140 A | 3/2000 | Schwartz et al. | |
| 6,042,610 A | 3/2000 | Li et al. | |
| 6,051,750 A | 4/2000 | Bell | |
| 6,056,752 A | 5/2000 | Roger | |
| 6,056,777 A | 5/2000 | McDowell | |
| 6,056,778 A | 5/2000 | Grafton et al. | |
| 6,060,640 A * | 5/2000 | Pauley et al. | 623/23.72 |
| 6,066,160 A | 5/2000 | Colvin et al. | |
| 6,068,648 A | 5/2000 | Cole et al. | |
| 6,077,989 A * | 6/2000 | Kandel et al. | 623/13.17 |
| 6,080,194 A * | 6/2000 | Pachence et al. | 623/23.76 |
| 6,093,201 A | 7/2000 | Cooper et al. | |
| 6,098,347 A | 8/2000 | Jaeger et al. | |
| 6,099,567 A | 8/2000 | Badylak et al. | |
| 6,110,212 A * | 8/2000 | Gregory | 623/23.72 |
| 6,126,686 A | 10/2000 | Badylak et al. | |
| 6,132,465 A * | 10/2000 | Ray et al. | 623/17.16 |
| 6,133,325 A | 10/2000 | Schwartz et al. | |
| 6,146,385 A | 11/2000 | Torrie et al. | |
| 6,152,935 A | 11/2000 | Kammerer et al. | |
| 6,153,292 A | 11/2000 | Bell et al. | |
| 6,156,044 A | 12/2000 | Kammerer et al. | |
| 6,165,225 A * | 12/2000 | Antanavich et al. | 623/23.72 |
| 6,171,344 B1 | 1/2001 | Atala | |
| 6,176,880 B1 | 1/2001 | Plouhar et al. | |
| 6,179,840 B1 | 1/2001 | Bowman | |
| 6,179,872 B1 | 1/2001 | Bell et al. | |
| 6,187,039 B1 | 2/2001 | Hiles et al. | |
| 6,190,414 B1 * | 2/2001 | Young et al. | 623/17.15 |
| 6,197,296 B1 | 3/2001 | Davies et al. | |
| 6,206,931 B1 | 3/2001 | Cook et al. | |
| 6,214,048 B1 | 4/2001 | Ito et al. | |
| 6,214,049 B1 | 4/2001 | Gayer et al. | |
| 6,224,892 B1 | 5/2001 | Searle | |
| 6,235,057 B1 | 5/2001 | Roger et al. | |
| 6,242,247 B1 * | 6/2001 | Rieser et al. | 435/297.1 |
| 6,251,143 B1 | 6/2001 | Schwartz et al. | |
| 6,251,876 B1 | 6/2001 | Bellini et al. | |
| 6,258,124 B1 * | 7/2001 | Darois et al. | 623/14.13 |
| 6,264,702 B1 * | 7/2001 | Ory et al. | 623/23.75 |
| 6,265,333 B1 * | 7/2001 | Dzenis et al. | 442/346 |
| 6,267,957 B1 | 7/2001 | Green et al. | |
| 6,270,530 B1 * | 8/2001 | Eldridge et al. | 623/23.74 |
| 6,273,893 B1 | 8/2001 | McAllen, III et al. | |
| 6,280,473 B1 * | 8/2001 | Lemperle et al. | 623/16.11 |
| 6,280,474 B1 | 8/2001 | Cassidy et al. | |
| 6,283,980 B1 | 9/2001 | Vibe-Hansen et al. | |
| 6,288,043 B1 | 9/2001 | Spiro et al. | |
| 6,290,711 B1 * | 9/2001 | Caspari et al. | 606/232 |
| 6,293,961 B2 | 9/2001 | Schwartz et al. | |
| 6,294,041 B1 * | 9/2001 | Boyce et al. | 156/275.5 |
| 6,299,905 B1 | 10/2001 | Peterson et al. | |
| 6,306,156 B1 | 10/2001 | Clark | |
| 6,306,159 B1 | 10/2001 | Schwartz et al. | |
| 6,306,177 B1 | 10/2001 | Felt et al. | |
| 6,319,258 B1 | 11/2001 | McAllen, III et al. | |
| 6,319,271 B1 | 11/2001 | Schwartz et al. | |
| 6,326,025 B1 | 12/2001 | Sigler et al. | |
| 6,333,029 B1 | 12/2001 | Vyakarnam et al. | |
| 6,334,872 B1 | 1/2002 | Termin et al. | |
| 6,355,699 B1 | 3/2002 | Vyakarnam et al. | |
| 6,358,284 B1 * | 3/2002 | Fearnot et al. | 623/23.72 |
| 6,364,884 B1 | 4/2002 | Bowman et al. | |
| 6,371,958 B1 | 4/2002 | Overaker | |
| 6,379,367 B1 | 4/2002 | Vibe-Hansen et al. | |
| 6,379,710 B1 | 4/2002 | Badylak | |
| 6,383,221 B1 * | 5/2002 | Scarborough et al. | 623/17.11 |
| 6,387,693 B2 | 5/2002 | Rieser et al. | |
| 6,402,766 B2 | 6/2002 | Bowman et al. | |
| 6,409,764 B1 * | 6/2002 | White et al. | 623/16.11 |
| 6,423,073 B2 | 7/2002 | Bowman | |
| 6,436,110 B2 | 8/2002 | Bowman et al. | |
| 6,440,444 B2 * | 8/2002 | Boyce et al. | 424/422 |
| 6,447,517 B1 | 9/2002 | Bowman | |
| 6,451,032 B1 * | 9/2002 | Ory et al. | 606/151 |
| 6,458,158 B1 * | 10/2002 | Anderson et al. | 623/16.11 |
| 6,458,383 B2 * | 10/2002 | Chen et al. | 424/451 |
| 6,464,729 B1 * | 10/2002 | Kandel | 623/23.63 |
| 6,497,650 B1 * | 12/2002 | Nicolo | 600/37 |
| 6,497,707 B1 | 12/2002 | Bowman et al. | |
| 6,508,821 B1 | 1/2003 | Schwartz et al. | |
| 6,517,564 B1 * | 2/2003 | Grafton et al. | 606/213 |
| 6,566,345 B2 | 5/2003 | Miller et al. | |
| 6,572,650 B1 * | 6/2003 | Abraham et al. | 623/1.38 |
| 6,592,623 B1 | 7/2003 | Bowlin et al. | 623/14.13 |
| 6,602,291 B1 * | 8/2003 | Ray et al. | 623/17.11 |
| 6,638,312 B2 * | 10/2003 | Plouhar et al. | 623/23.72 |
| 6,652,872 B2 * | 11/2003 | Nevo et al. | 424/423 |
| 6,666,892 B2 * | 12/2003 | Hiles et al. | 623/23.72 |
| 6,692,499 B2 * | 2/2004 | Tormala et al. | 606/72 |
| 6,743,255 B2 * | 6/2004 | Ferree | 623/17.11 |
| 6,812,221 B2 * | 11/2004 | McKeehan et al. | 514/56 |
| 6,840,962 B1 * | 1/2005 | Vacanti et al. | 623/23.76 |
| 6,869,938 B1 | 3/2005 | Schwartz et al. | |
| 6,989,034 B2 | 1/2006 | Hammer et al. | |
| 2001/0002446 A1 | 5/2001 | Plouhar et al. | |
| 2001/0023373 A1 | 9/2001 | Plouhar et al. | |
| 2001/0024658 A1 * | 9/2001 | Chen et al. | 424/452 |
| 2001/0043943 A1 * | 11/2001 | Coffey | 424/447 |
| 2002/0019649 A1 | 2/2002 | Sikora et al. | |
| 2002/0031551 A1 | 3/2002 | Peterson et al. | |
| 2002/0034533 A1 | 3/2002 | Peterson et al. | |
| 2002/0038151 A1 * | 3/2002 | Plouhar et al. | 623/23.72 |
| 2002/0048595 A1 | 4/2002 | Geistlich et al. | |
| 2002/0052628 A1 | 5/2002 | Bowman | |
| 2002/0095157 A1 | 7/2002 | Bowman | |
| 2002/0099448 A1 | 7/2002 | Hiles | |
| 2002/0147497 A1 * | 10/2002 | Belef et al. | 623/17.12 |
| 2002/0156400 A1 * | 10/2002 | Babaev | 601/2 |
| 2002/0165611 A1 | 11/2002 | Enzerink et al. | |
| 2002/0169465 A1 | 11/2002 | Bowman et al. | |
| 2002/0173806 A1 | 11/2002 | Giannetti et al. | |
| 2002/0190136 A1 * | 12/2002 | Babaev | 239/102.2 |
| 2003/0014126 A1 * | 1/2003 | Patel et al. | 623/23.72 |
| 2003/0021827 A1 * | 1/2003 | Malaviya et al. | 424/424 |
| 2003/0023316 A1 * | 1/2003 | Brown et al. | 623/23.72 |
| 2003/0032961 A1 * | 2/2003 | Pelo et al. | 606/72 |
| 2003/0033021 A1 * | 2/2003 | Plouhar et al. | 623/23.57 |
| 2003/0033022 A1 * | 2/2003 | Plouhar et al. | 623/23.57 |
| 2003/0036797 A1 * | 2/2003 | Malaviya et al. | 623/14.12 |
| 2003/0036801 A1 * | 2/2003 | Schwartz et al. | 623/23.63 |
| 2003/0044444 A1 * | 3/2003 | Malaviya et al. | 424/423 |
| 2003/0049299 A1 * | 3/2003 | Malaviya et al. | 424/423 |
| 2003/0078617 A1 | 4/2003 | Schwartz et al. | |
| 2003/0212447 A1 * | 11/2003 | Euteneuer et al. | 623/1.2 |
| 2004/0059431 A1 | 3/2004 | Plouhar et al. | |
| 2004/0143344 A1 * | 7/2004 | Malaviya et al. | 623/23.72 |
| 2004/0166169 A1 | 8/2004 | Malaviya et al. | |
| 2004/0220574 A1 | 11/2004 | Pelo et al. | |
| 2005/0027307 A1 | 2/2005 | Schwartz et al. | |
| 2005/0249771 A1 | 11/2005 | Malaviya et al. | |
| 2005/0249772 A1 | 11/2005 | Malaviya et al. | |

FOREIGN PATENT DOCUMENTS

| | | |
|---|---|---|
| EP | 0 591 991 A2 | 4/1994 |
| EP | 0 632 999 A1 | 11/1995 |
| EP | 0734736 A1 | 2/1996 |
| EP | 1593400 | 11/2005 |
| GB | 2215209 | 9/1989 |
| JP | 11319068 | 11/1999 |
| WO | 90/09769 | 9/1990 |
| WO | 94/11008 | 5/1994 |

| WO | 95/05083 | 2/1995 |
| WO | 95/22301 | 8/1995 |
| WO | 95/06439 | 9/1995 |
| WO | 95/32623 | 12/1995 |
| WO | 96/24661 | 8/1996 |
| WO | WO97/05193 | 2/1997 |
| WO | 97/37613 | 10/1997 |
| WO | 98/06445 | 2/1998 |
| WO | 98/22158 A2 | 5/1998 |
| WO | 98/22158 A3 | 5/1998 |
| WO | 98/30167 | 7/1998 |
| WO | 98/34569 | 8/1998 |
| WO | WO 98/40111 | 9/1998 |
| WO | 99/03979 | 1/1999 |
| WO | 99/43786 | 9/1999 |
| WO | 99/47188 | 9/1999 |
| WO | WO-99/62439 A1 * | 12/1999 |
| WO | 00/16822 | 3/2000 |
| WO | WO 00/15765 | 3/2000 |
| WO | 00/24437 A2 | 5/2000 |
| WO | 00/24437 A3 | 5/2000 |
| WO | 00/32250 | 6/2000 |
| WO | 00/48550 | 8/2000 |
| WO | 00/72782 | 12/2000 |
| WO | 01/19423 | 3/2001 |
| WO | 01/39694 A2 | 6/2001 |
| WO | 01/39694 A3 | 6/2001 |
| WO | 01/45765 | 6/2001 |
| WO | 01/66159 | 9/2001 |
| WO | WO 02/22184 | 3/2002 |
| WO | WO 03/007784 | 1/2003 |
| WO | WO03/007788 | 1/2003 |
| WO | WO03/007790 | 1/2003 |

OTHER PUBLICATIONS

Sandusky, et al., "Healing Comparison of Small Intestine Submucosa and ePTFE Grafts in the Canine Carotid Artery", *J. Surg.Res.*, 58:415-420, (1995).
Knapp, et al., "Biocompatibility of Small-Intestine Submucosa in Urinary Tract as Augmentation Cystoplasty Graft and Injectable Suspension", *J Endourology*, 8:125-130, (1994).
Kropp at al., "Regenerative Bladder Augmentation: A Review of the Initial Preclinical Studies with Porcine Small Intestinal Submucosa", *Muscle, Matrix, and Bladder Function*. Plenum Press, New York, (1995).
Kropp et al., "Experimental Assessment of Small Intestinal Submucosa as a Bladder Wall Substitute", *Urology* 446:396-400, (1995).
Vaught et al., "Detrusor Regeneration in the Rat Using Porcine Small Intestinal Submucosa Grafts: Functional Innervation and Receptor Expression", *J. Urol.*, 155:374-378, (1996).
Kropp et al, Characterization of Small Intestinal Submucosa Regenerated Canine Detrusor: Assessment of Reinnervation, In Vitro Compliance and contractility, *J. of Urol*,156:599-607, (1996).
Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).
Aiken et al., "Small Intestinal Submucosa as an Intra-Articular Ligamentous Graft Material: A Pilot Study in Dogs", *Vet Comp Orthopedics Traumatology*, 7:124-128, (1994).
Badylak et al., "The Use of Xenogeneic Small Intestinal Submucosa as a Biomaterial for Achille's Tendon Repair in a dog model", *J Biomed Materials*, 29:977-985, (1995).
Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).
Ferrand et al., "Directional Porosity of Porcine Small-Intestinal Submucosa", *J Biomed Materials Res*, 27:1235-1241, (1993).
Hiles et al., "Porosity of Porcine Small-Intestinal Submucosa for use as a Vascular Graft", *J Biomed Materials Res*, 27: 139-144, (1993).

Hodde et al., "Glycosaminoglycan Content of Small Intestinal Submucosa: A Bioscaffold for Tissue Replacement", *Tissue Engineering*, 2:3, 209-217, (1996).
Prevel et al., "Small Intestinal Submucosa: Utilization for Repair of Rodent Abdominal Wall Defects", *Ann Plast Surg*, 35:374-380, (1995).
Clarke et al., "Intestine Submucosa and Polypropylene Mesh for Abdominal Wall Repair in Dogs", *J Surg Res*, 60:107-114, (1996).
Prevel et al., "Small Intestinal Submucosa: Utilization as a Wound Dressing in Full-Thickness Rodent Wounds", *Ann Plast Surg.* 35:381-388, (1995).
Cobb et al., "Histology after Dural Grafting with Small Intestinal Submucosa", *Surgical Neurology*, 46: 389-394, (1998).
Cobb et al., "Porcine Small Intestinal Submucosa as a Dural Substitute", *Surgical Neurology*, 51:99-104. (1999).
Voytik-Harbin et al., "Application and Evaluation of the AlamarBlue Assay for Cell Growth and Survival of Fibroblasts", *Journal of Immunological Methods*, In Vitro *Cell Bio-Animal*, 34: 2399-246, (1998).
Suckow, M.A., "Enhanced Bone Regeneration Using Porcine Small Intestinal Submucosa", *J. Invest Surg*, 12: 277, (1999).
Badylak , S., et al., "Naturally Occurring Extracellular Matrix as a Scaffold for Musculoskeletal Repair", *Clin Orthop*, 3675:S333-S3433, (1999).
Cook, J.L. et al., "Induction of Meniscal Regeneration in Dogs Using a Novel Biomaterial", *Am J Sports Med*, 27: 658, (1999).
Dejardin, L.M. et al., "Use of small intestinal submucosal implants for regeneration of large fascial defects: an experimental study in dogs", J Biomed Mater Res, 46:203-211, (1999).
Sacks, M.S., et al., "Quantification of the fiber architecture and biaxial mechanical behavior of porcine intestinal submucosa", *J Biomed Mater Res*, 46:1-10, (1999).
COOK® News Releases, "COOK® Introduces Innovative Surgisis™ Soft Tissue Repair Biomaterial", (May 21, 2000).
COOK® News Releases, "COOK® Oasis™ Wound Dressing Biomaterial From COOK® Remodels Partial Thickness Skin Injuries", (Dec. 23, 1999).
COOK® News Releases, "Cook Incorporated Forms Dedicated Tissue Engineered Products Group", (Feb. 16, 2000).
COOK® News Releases, "FDA Clears Oasis™ Wound Dressing Biomaterial From COOK® for Full-Thickness Skin Injuries", (Jan. 24, 2000).
Klootwyk, et al., "The Use of Xenographic SIS as a Biomaterial for Achilles Tendon Repair in Dogs," First SIS Symposium, Dec. 1996, USA.
Lenz, et al., "SIS as an ACL Replacement in Dogs and Goats," First Symposium, Dec. 1996, USA.
Cook, et al., "Comparison of SIS Cancellous Bone as Substrates for Three-Dimensional Culture of Canine Articular Chondrocytes," First SIS Symposium, Dec. 1996, USA.
Badylak, et al., "Different Configurations of Small Intestinal Submucosa as a Biomaterial for Achilles Tendon Repair in a Dog Model," First SIS Symposium, Dec. 1996, USA.
Voytik-Harbin & Badylak, "Induction of Osteogenic Activity By Small Intestinal Submucosa in Rat Calvaria Non-union Defects,"First SIS Symposium, Dec. 1996, USA.
Kandel, et al., "SIS and Reconstituted Cartilage and Its Use in Joint Resurfacing of Focal Defects in Rabbits," First SIS Symposium, Dec. 1996, USA.
Tullius, et al., "Differential Permeabilty of SIS," First SIS Symposium, Dec. 1996, USA.
Obermiller, et al., "Suture Retention Strength of SIS," First SIS Symposium, Dec. 1996, USA.
Shelton, et al., "Repair of the Canine Medial Meniscus using SIS: A Feasibility Study," Second SIS Symposium, Dec. 1998, USA.
Cook, et al., "Meniscal Regeneration in dogs Using Grafts of SIS," Second SIS Symposium, Dec. 1998, USA.
Welch, et al., "Healing of Canine Meniscal Defect with Small Intestinal Submucosa Implants," Dec. 1998, USA.
Solchaga, et al., "SIS as Delivery Vehicle for Mesenchymal Progenitor Cells," Dec. 1998, USA.
Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates The Differentiation of Myofibroblasts," Third SIS Symposium, Nov. 2000, USA.

Cook, et al., "Tissue Engineering For Meniscal Repair Using SIS," Third SIS Symposium, Nov. 2000, USA.

Lifrak, et al., "Enhanced Repair of Goat Meniscal Defects Using Porcine Small Intestinal Submucosa (SIS)," Third SIS Symposium, Nov. 2000, USA.

Hoffman, "SIS Disc Replacement For the Temporomandibular Joint," Third SIS Symposium, Nov. 2000, USA.

Kaeding, "Use of SIS in The Surgical Treatment of Chronic Symptomatic Patella Tendinosis," Third SIS Symposium, Nov. 2000, USA.

Tomczak and Kaeding, "Use of SIS in The Surgical Treatment of Tendinosis About The Foot And Ankle," Third SIS Symposium, Nov. 2000, USA.

Moore, et al., "Bridging Segmental Defects in Long Bones With Intramedullary Tubes and Periosteal Sleeves Made From Small Intestinal Submucosa (SIS)," Third SIS Symposium, Nov. 2000, USA.

Wang, et al., "Small Intestinal Submucosa Enhances Healing of Medical Collateral Ligament in a Rabbit Model," Third SIS Symposium, Nov. 2000, USA.

Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of The Porcine Small Intestine Submucosal Tissue Graft and Repair of Rotator Cuff Tears," Third SIS Symposium, Nov. 2000, USA.

"Small Intestinal Submucosa," Third SIS Symposium, Nov. 2000, USA.

"Current Clinical Applications of SIS," Third SIS Symposium, Nov. 2000, USA.

Hodde, et al., "Glycosaminoglycan Content of Small Intestinal Submucosa: A Potential for GAG-Growth Interactions in SIS-Mediated Healing", First Symposium, Dec. 1996, USA.

Friess, "Collagen in drug delivery and tissue engineering", Advanced Drug Delivery Reviews, vol. 55, No. 12, 2003, pp. 1529-1530.

Olsen et al., "Recombinant collagen and gelatin for drug delivery", Advanced Drug Delivery Reviews, vol. 55, No. 12, 2003, pp. 1547-1567.

Aigner et al., "Collagens-major component of the physiological cartilage matrix, major target of cartilage degeneration, major tool in cartilage repair", Advanced Drug Delivery Reviews, vol. 55, No. 12, 2003, pp. 1569-1593.

Geiger et al., "Collagen sponges for bone regeneration with rhBMP-2", Advanced Drug Delivery Reviews, vol. 55, No. 12, 2003, pp. 1613-1629.

Ruszczak et al., "Collagen as a carrier for on-site delivery of antibacterial drugs", Advanced Drug Delivery Reviews, vol. 55, No. 12, 2003, pp. 1679-1698.

O'Grady et al., "Global regulatory registration requirements for collagen-based combination products: points to consider", Advanced Drug Delivery Reviews, vol. 55, No. 12, 2003, pp. 1699-1721.

Matthews et al., "Electrospinning of Collagen Type II: A Feasibility Study", Journal of Bioactive and Compatible Polymers, vol. 18, Mar. 2003, pp. 125-134.

Biscarini et al., "Growth of High Vacuum Sublimed Oligomer Thin Films", ACS Polymer Preprints, vol. 37, No. 2, 1996, pp. 618-619.

Biscarini et al., "Morphology and roughness of high-vacuum sublimed oligomer thin films", Thin Solid Films, vol. 439-443, 1996, pp. 284-285.

Bisccarini et al., "Scaling Behavior of Anisotropic Organic Thin Films Grown in High-Vacuum", Physical Review Letters, vol. 78, No. 12, Mar. 24, 1997, pp. 2389-2392.

Voytik-Harbin et al., "Identification of Extractable Growth Factors from Small Intestinal Submucosa", Journal of Cellular Biochemistry, vol. 67, 1997, pp. 478-491.

McPherson, Ph.D. et al., "Characterization of Fibronectin Derived from Porcine Small Intestinal Submucosa", Tissue Engineering, vol. 4, No. 1, 1998, pp. 75-83.

Hodde, et al., "Vascular Endothelial Growth Factor in Porcine-Derived Extracellular Matrix", Endothelium, vol. 8(1), 2001, pp. 11-24.

Hodde et al., "Wounds: A Compendium of Clinical Research and Practice", Website: http:www.hmpcommunications.com/WNDS, Printed: Jul. 12, 2005, 7 pgs.

Hurst et al., "Mapping of the distribution of significant proteins and proteoglycans in small intestinal submucosa by fluorescence microscopy", J. Biomater. Sci. Polymer Edn., vol. 12, No. 11, 2001, pp. 1267-1279.

Hodde et al., "Fibronectin peptides mediate HMEC adhesion to porcine-derived extracellular matrix", Biomaterials, vol. 23, 2002, pp. 1841-1848.

Hodde, "Naturally Occurring Scaffolds for Soft Tissue Repair and Regeneration", Tissue Engineering, vol. 8, No. 2, 2002, pp. 295-308.

Allman et al., Xenogeneic Extracellular Matrix Grafts Elicit a Th2-Restricted Immune Response, Transplantation, vol. 71, No. 11, Jun. 15, 2001, pp. 1631-1640.

Krcma, "Nonwoven Textiles", Textile Trade Press, Manchester, England, 1962, 6 pgs.

Answers.com definition of "freeze-dry" accessed May 12, 2005. 6 pages.

Ma and Zhang, 2001, "Microtublar Architecture of Biodegradable Polymer Scaffolds," J Biomed Mater Res, 56(4), pp. 469-477.

Ma and Choi, 2001 "Biodegradable Polymer Scaffolds with Well-Defined Interconnected Spherical Pore Network," Tissue Eng, 7(1), pp. 23-33.

Klawitter et al., 1976, "An Evaluation of Bone Growth into Porous High Density Polyethylene," J Biomed Mater Res, 10(2), pp. 311-323.

White and Shors, 1991, "Biomaterial Aspects of Interpore-200 Porous Hydroxyapatite," Dent Clin North Am, 30, pp. 49-67.

Shors, 1999, "Coralline Bone Graft Substitutes," Orthop Clin North Am, 30(4), pp. 599-613.

Wang, 1990, "Experimental Study of Osteoganic Activity of Sintered Hydroxyapatite -On the Relationship of Sintering temperature and Pore Size," Nippon Seikeigeka Gakki Zasshi, 64(9), pp. 847-859.

Nehrer et al., 1997, "Matrix collagen type and pore size influence behaviour of seeded canine chondrocytes," Biomaterials, 18(11), pp. 769-776.

Salem et al., 2002, "Interactions of 3T3 fibroblasts and endothelial cells with defined pore features," J. Biomed Mater Res, 61(2):212-217.

Definitions of "intertwine" and "twine", American Heritage Dictionary of the English Language Online, Accessed Sep. 29, 2005, 2 pgs.

How to Cut Meat Products 2001, Urschel Corp., Assessed online at fr.urschel.com/literature/HTCMeat.pdf on Oct. 3, 2005, 8 pgs.

Definitions of "comminute" and "slurry", Dictionary.com; Accessed Sep. 20, 2005, 2 pgs.

P. K. Chu et al., "Plasma-surface modification of biomaterials", Materials Science and Engineering, Reports: A Review Journal, vol. 36, No. 5-6, Mar. 29, 2002, pp. 143-206.

Arnoczky et al., The microvasculature of the meniscus and its response to injury—An experimental study in the dog, Am. J. Sports Med., 1983, 11(3); pp. 131-141.

Fox et al., "Trephination of incomplete meniscal tears," Arthroscopy, 1993, 9(4); pp. 451-455.

Arnoczky et al., Meniscal repair using an exogenous fibrin clot—An experimental study of dogs, J. Bone Joint Surg. Am., 1988, 70(8), pp. 1209-1217.

Rodeo, "Arthroscopic meniscal repair with use of the outside-in technique", Instr. Course Lect., 2000, 49, pp. 195-206.

Stollsteimer et al., "Meniscal allograft transplantation: a 1- to 5-year follow-up of 22 patients", Arhroscopy, 2000, 16(4), pp. 343-347.

Rodeo, "Meniscal allografts—where do we stand?", Am. J. Sports Med., 2001, 29(2), pp. 246-261.

Sweigart et al., "Toward tissue engineering of the knee meniscus", Tissue Eng., 2001, 7(2), pp. 111-129.

Boss et al., "Technical Innovation: creation of a peripheral vascularized trough to enhance healing in cryopreserved meniscal allograft reconstruction", Knee Surg Sports Traumatol Arthrosc., 2000, 8(3), pp. 159-162.

Siegel et al., "Meniscal allografts", Ciin Sports Med., 1993, 12(1), pp. 59-80.

Klompmaker et al., "Meniscal replacement using a porous polymer prosthesis: a preliminary study in the dog."; Blomaterials. 1996, 17(12), pp. 1169-1175.

de Groot et al., "Use of porous polyurethanes for meniscal reconstruction and meniscal protheses", Biomaterials, 1996, 17(2), pp. 163-173.

Spaans et al, "Solvent-free fabrication of micro-porous polyurethane amide and polyurethane-urea scaffolds for repair and replacement of the knee-joint meniscus", Biomaterials, 2000, 21(23), pp. 2453-2460.

Stone et al., "Regeneration of meniscal cartilage with use of a collagen scaffold—Analysis of Preliminary data", J. Bone Joint Surg. Am., 1997, 79(12), pp. 1770-1777.

Rodkey et al., "A clinical study of collagen meniscus implants to restore the injured meniscus", Clin. Orthop., 1999, 49(367 Suppl.), pp. S281-S292.

Merriam-Webster Online Dictionary definitions of "suspension", "suspend", "cohesive", "cohesion", "comminute", "pulverize", "submucosa", and "tissue". Accessed Mar. 30, 2006, 9 pgs.

Resin Technology Group, LLC, "Viscosity chart", http://www.resintechgroup.com/tables/viscosity.html, accessed online Mar. 30, 2006, 1pg.

Definitions from Onelook.com for "trimethylen" and "trimethylene," Mar. 17, 2006, 1 page.

DiSilvestro et al., "Effects of Cross-Linking on the Mechanical Properties of a Porous Foam Scaffold of Small Intestine Submucosa", Society for Biomaterials 29$^{th}$ Annual Meeting Transactions, 2003, pp. 88.

J.S. Pieper et al "Preparation and characterization of porous crosslinked collagenous matrices containing bioavailable chondroltin suplhate" Biomaterials 1999, 20; 847-858.

P.B. van Wachern et al. "In vivo biocompatability of carbodiimide-crosslinked collagen matrices: Effects of crosslink density, heparin immobilization, and bFGF loading" J. Biomed. Mater. Res. 2001, 55 (3): 368-378.

Kyumin Whang "A biodegradable polymer scaffold for delivery of osteotropic factors" Biomaterials 2000, 21 (24): 2545-2551.

J.S. Pieper et al. Attachment of glycosaminoglycans to collangenous matrices modulates the tissue response in rats, Biomaterials 2000, 21 (16): 1689-1699.

Kristen Billiar et al. "Effects of carbodiimde crosslinking conditions on the physical properties of laminated intestinal submucosa", J. Biomed. Mater. Res. 2001, 56(1): 101-108.

Toshimitsu Momose et al. "Surface modification of extrasynovial tendon by chemically modified hyaluronic acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989. 30 (1): 498.

The Encyclopedia of Polymer Science, 1988 (13) 31-41.

"Handbook of Biodegradable Polymers" Hardwood Press 1977 (161-182).

"Handbook of Biodegradable Polymers" Hardwood Press 1997 (99-118).

Allman et al., "The Th2-Restricted Immune Response to Xenogeneic Small Intestinal Submucosa Does Not Influence Systemic Protective Immunity to Viral and Bacterial Pathogens", Tissue Engineering, vol. 8, No. 1, 2002, pp. 53-62.

Chen et al., "Collagen Hybridization with Poly(l-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp. 53-61, 2004.

Cheng & Teoh, "Surface modification of ultra thin poly ($\epsilon$ caprolactone) fims using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp. 3757-3764, 2003.

Yang et al., "Effect of surface treatment on the biocompatibility of microbial polyhydroxyalkanoates", Biomaterials, v 23 (5), pp. 1391-1397, 2002.

Croll et al., "Controllable surface modification of Poly(lactic-co-glycolic acid) (PLGA) by hydrolysis or aminolysis I: physical, chemical, and theoretical aspects", *Biomacromolecules*, Mar.-Apr. 2004, 5(2): 463-473.

Kwon et al., "Fibroblast culture on surface-modified poly (glycolide-co- $\epsilon$-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, Feb. 17(12): 151-159.

Tan W, Krishnaraj R, Desai TA "Evaluation of nanostructured composite collagen-chitosan matrices for tissue engineering", Tissue Eng Apr: 7(2): 203-210, 2001.

Arnoczky SP "Building a meniscus", Biological considerations, Clin Orthop Oct; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11). pp. 33-39, 2003.

Zhang et al., Design of nanostructured biological materials through self-assembly of peptides and proteins, MIT Current Opinion in chemical Biology, 2002, 6:865-871.

Hodde and Hiles, "Bioactive FGF-2 in sterilized extracellular matrix", Wounds, 13(5): 195-201 (2001).

O,Meara, Patrick, "The basic science of meniscus repair," Orthopaedic review, Jun. 1993, pp. 681-686.

Clearfix screw advertisement, 1998, Innovasive devices, Inc.

Winters and Justin, "Clearfix meniscal screw", Innovasive devices, Inc. 1998.

Surgical dynamics, meniscal stapler advertisement, 1997.

Bionix implants, Meniscus arrow advertisement, 1996.

Instrumennt makar, inc., Meniscus mender II, 1989.

William G. Clancy, Jr., M.D., and Ben K. Graf, M.D., "Arthroscopic Meniscal Repair," ACUFEX Microsurigal Inc., advertisement, 1988.

\* cited by examiner

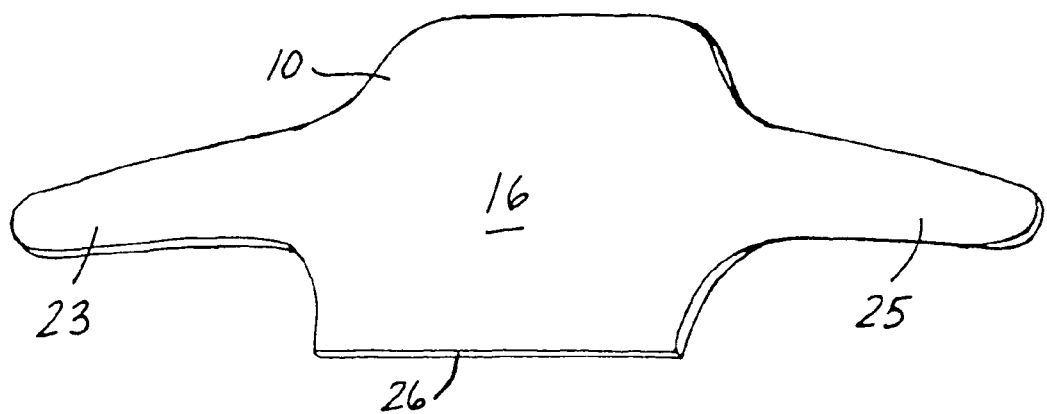
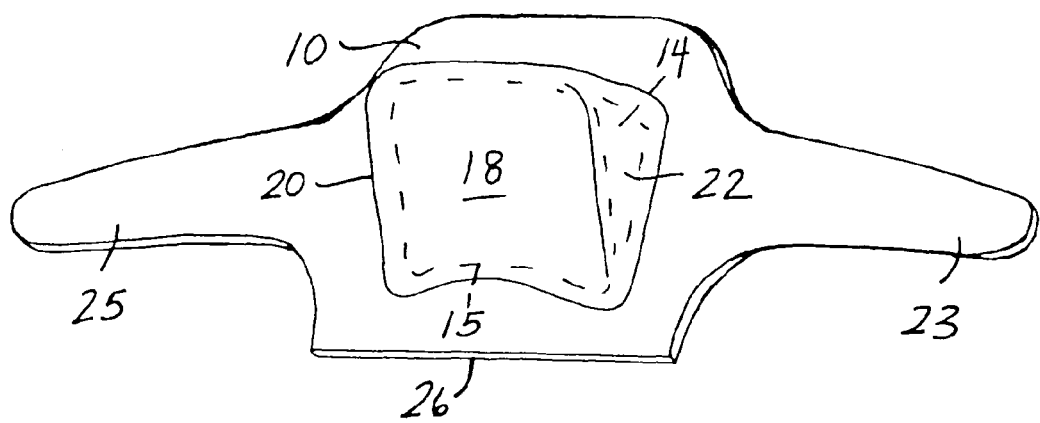
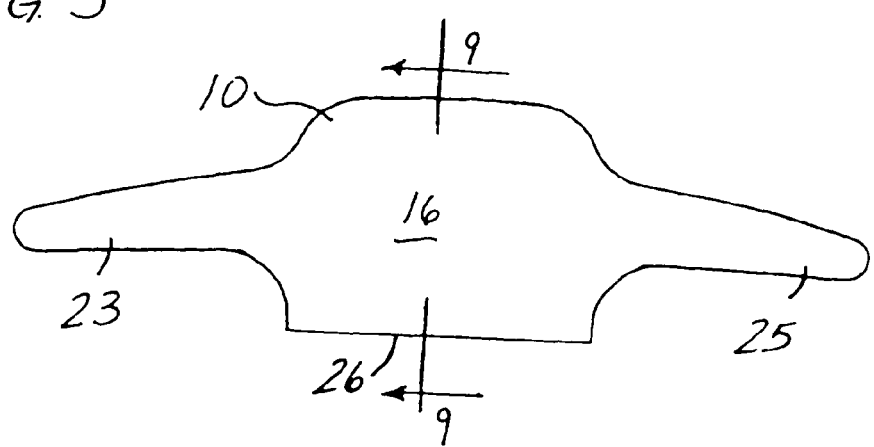

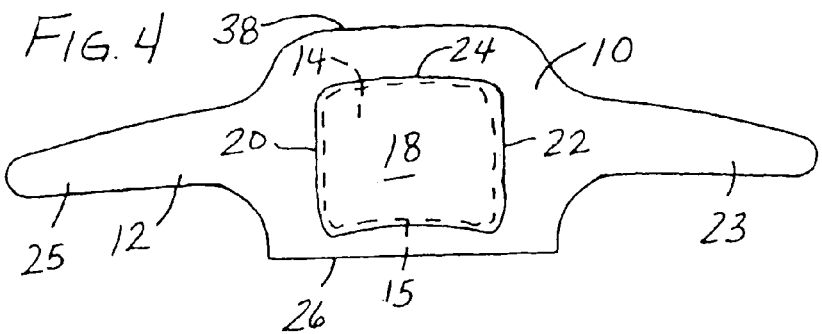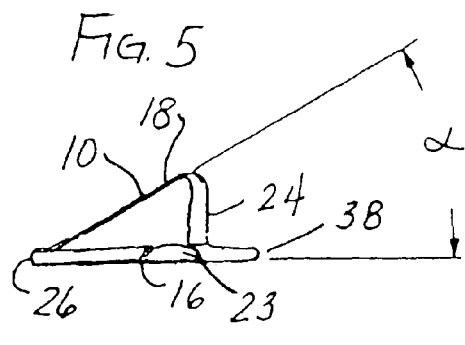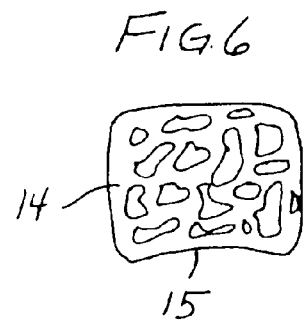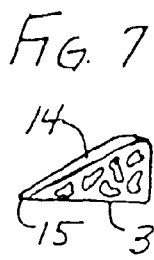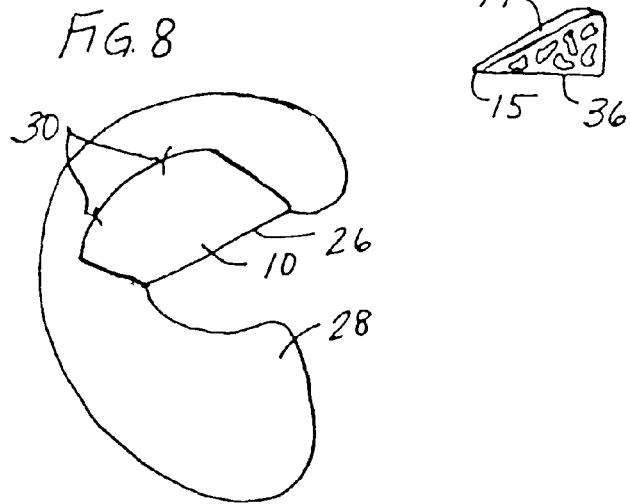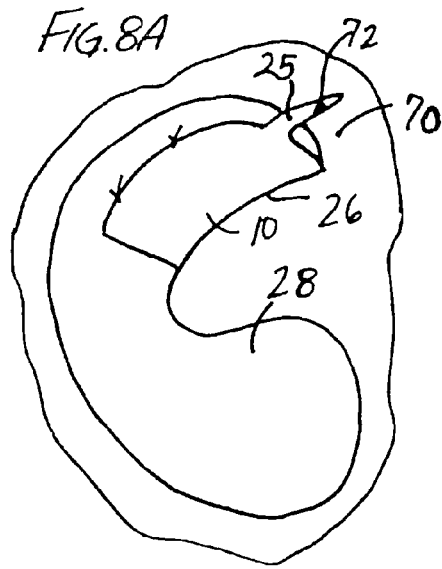

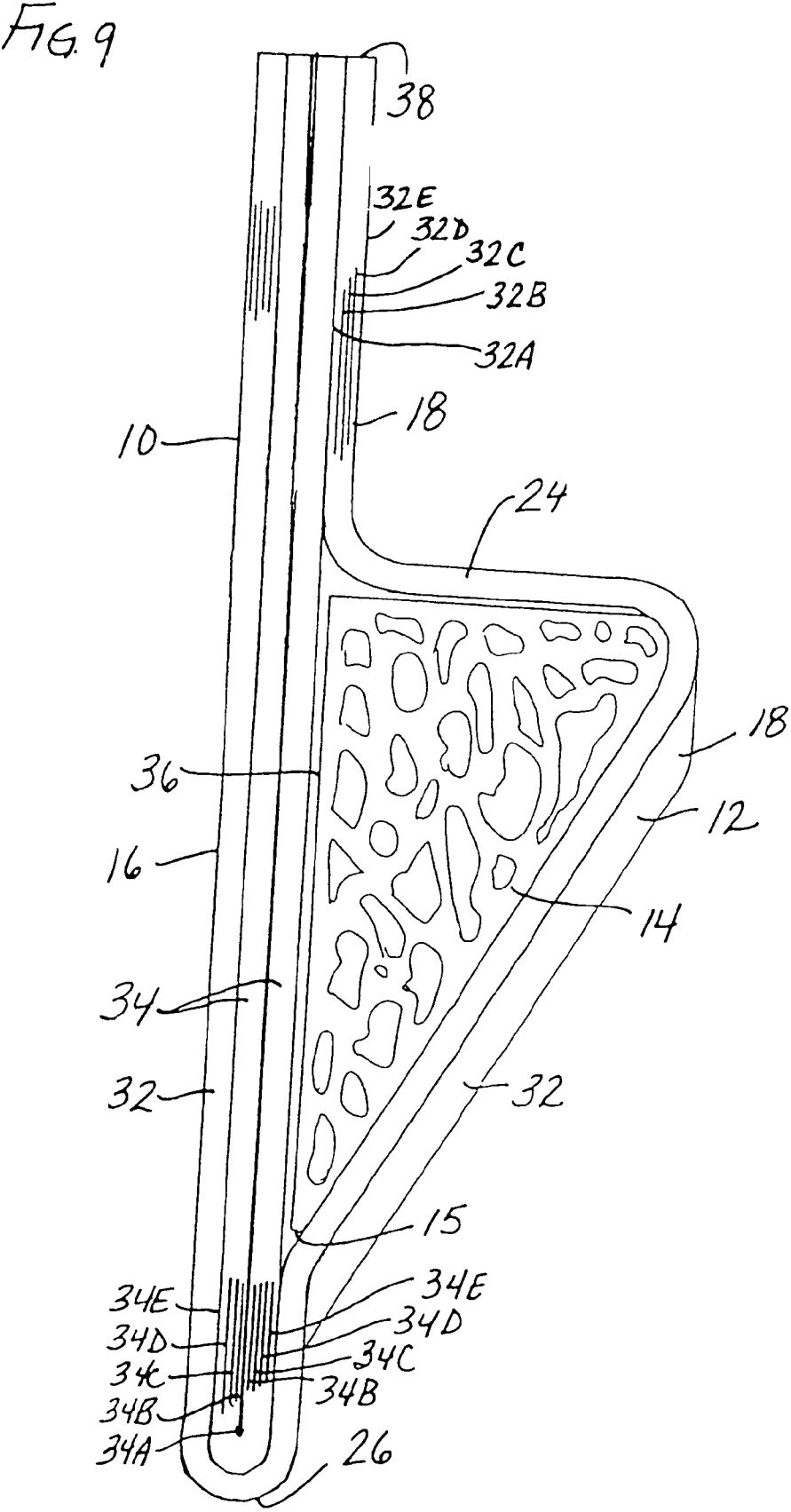

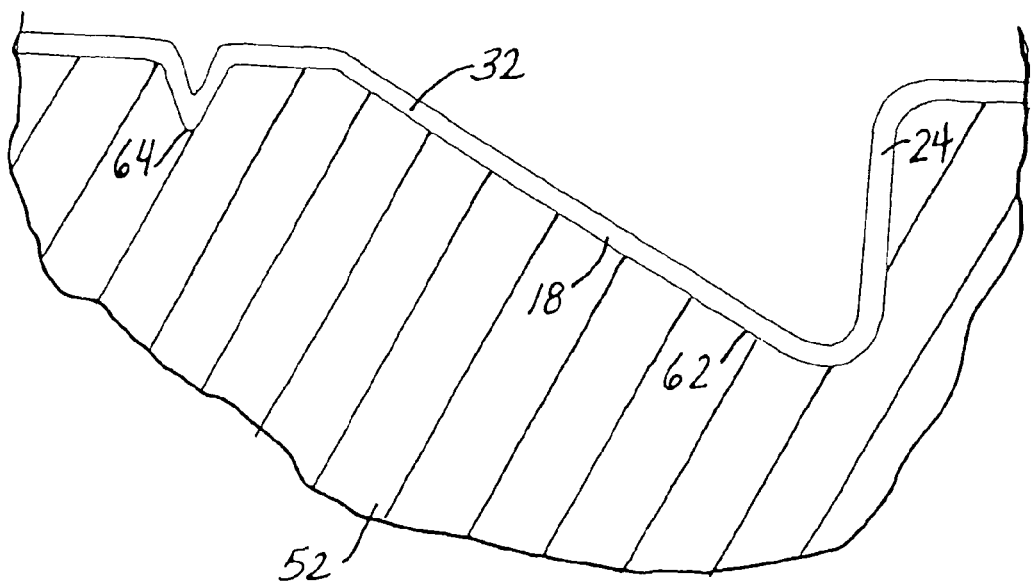
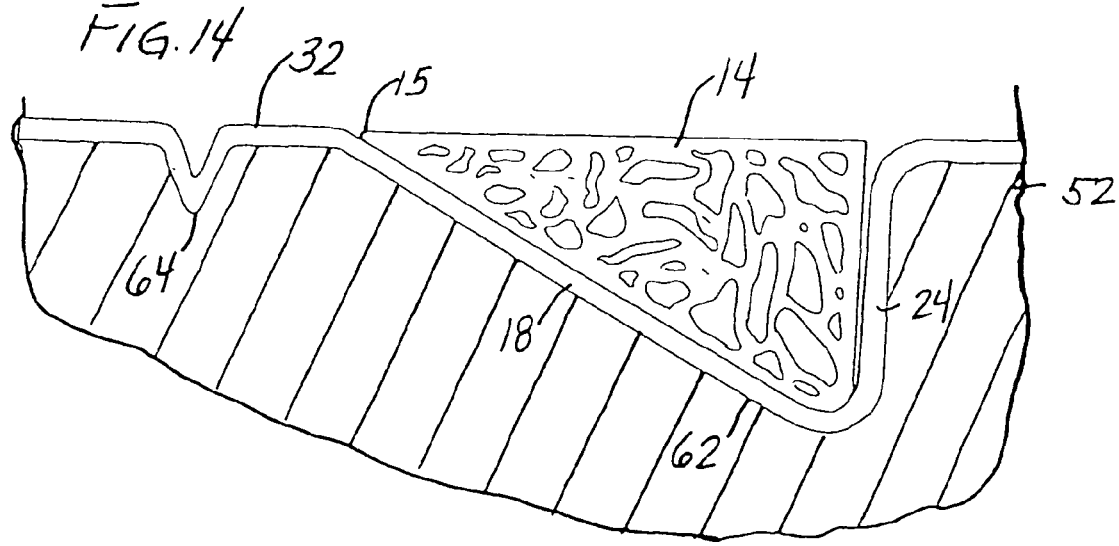

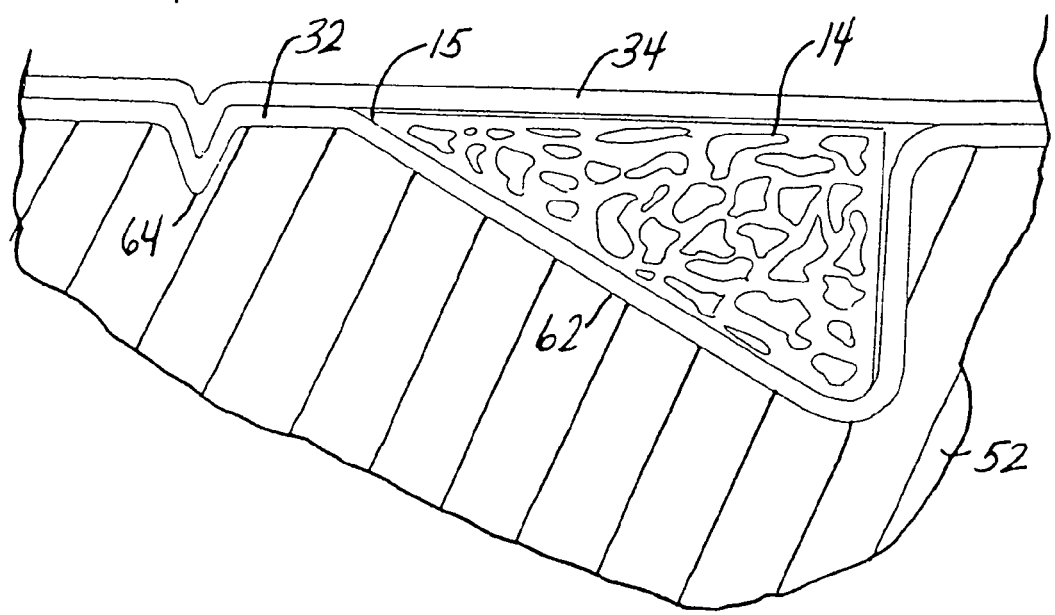
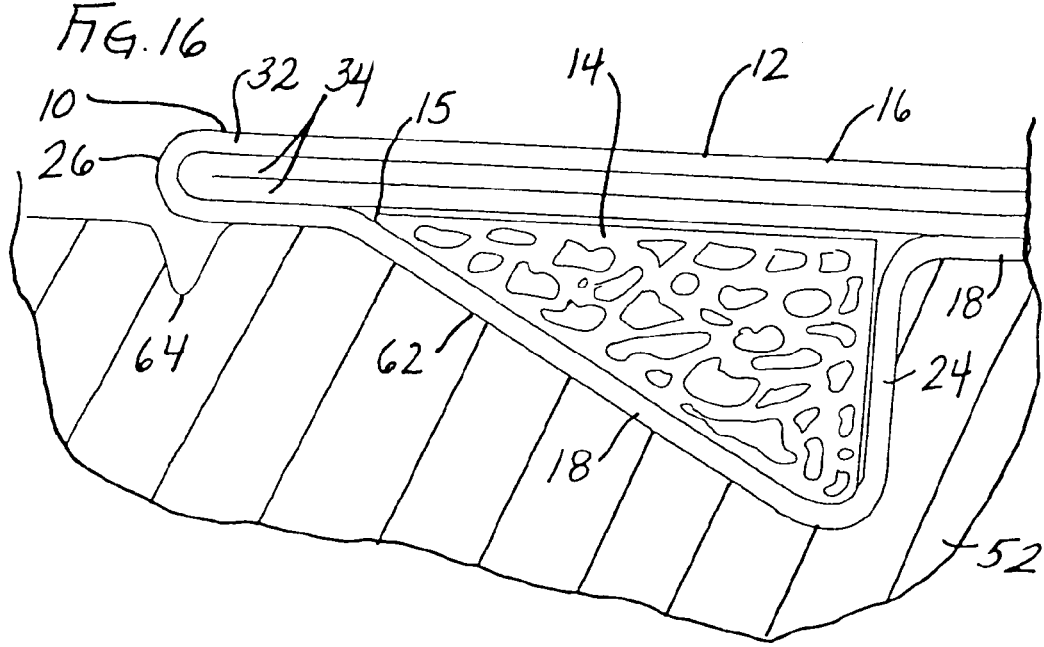

IMPLANTABLE TISSUE REPAIR DEVICE

This is a continuation-in-part of U.S. patent application Ser. No. 10/195,794, entitled "Meniscus Regeneration Device and Method", filed on Jul. 15, 2002 by Malaviya et al., which claims the benefit of U.S. Provisional Application Nos. 60/388,713, filed Jun. 14, 2002 and 60/305,786, filed on Jul. 16, 2001, which are incorporated by reference herein in their entireties.

FIELD OF THE INVENTION

The present invention relates generally to surgical devices or implants for repairing and regenerating damaged or diseased fibrocartilage, and to a method of making such devices.

BACKGROUND OF THE INVENTION

Articular cartilage is a type of hyaline cartilage that lines the surfaces of the opposing bones in a diarthrodal joint (e.g. knee, hip, shoulder, etc.). Articular cartilage provides a near frictionless articulation between the bones, while also functioning to absorb and transmit the compressive and shear forces encountered in the joint. Further, since the tissue associated with articular cartilage is aneural, these load absorbing and transmitting functions occur in a painless fashion in a healthy joint.

Human joints also have another type of cartilage present: intra-articular fibrocartilage. Intra-articular fibrocartilage can be present in the form of a discus articularis, that is, as a plate or ring of fibrocartilage in the joint capsule separating the joint surfaces (articular cartilage) of the bones of the joint. Such fibrocartilage is present, for example, in the temporomandibular joint, between vertebrae, and in the knee joint. In the knee joint, the intra-articular fibrocartilage comprises the meniscus, a crescent-shaped or semi-lunar-shaped disc of tissue that is located between the femoral condyles and the tibial plateau. The meniscus primarily functions as a shock absorber, absorbing the shock of compressive and shear forces in the knee. The meniscus also provides a substantially frictionless surface for articulation of the knee joint.

When cartilage tissue is no longer healthy, there can be debilitating pain in the joint. Cartilage health can be adversely affected by disease, aging, or trauma. The adverse effects of disease, aging and trauma can be in the form of a tear in the cartilage or in the form of a breakdown of the cartilage matrix.

In the knee, the meniscus is frequently damaged in twisting injuries. It is also damaged with repetitive impact over time. Meniscus degeneration can also occur by aging; as a person ages, the meniscus can become soft in places, so that even common motions like squatting can cause meniscal tears. Such degenerative or traumatic tears to the meniscus, which result in partial or complete loss of function, frequently occur in the white-white zone of the meniscus. Such tears result in unstable flaps of meniscal tissue in the knee joint causing, in the short term, severe joint pain and locking, and in the long term, a loss of mechanical function leading to osteoarthritis.

Common surgical procedures for treating meniscal damage include tear repairs and menisectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos.: 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint. And when the resected tissue is from the avascular, white-white zone, the meniscus has little potential for self-regeneration. Thus, removal of meniscal tissue from the avascular white-white zone can result in partial or permanent loss of meniscal tissue, making the joint susceptible to osteoarthritis.

Attempts have been made to regenerate meniscal tissue following a menisectomy. Previous attempts have included the use of surgical techniques and implants. The surgical techniques have been used to provide vascularity to the avascular region through synovial abrasion or by providing vascular access channels. Implants have included fibrin clot, meniscal allografts (see Stollsteimer, G. T., et al., "Meniscal allograft transplantation: a 1-to 5-year follow-up of 22 patients," Arthroscopy, 16(4): pp 343-7 (2000); Rodeo, S. A., "Meniscal allografts—where do we stand," Am J Sports Med, 29(2): pp. 246-61 (2001)), synthetic biodegradable polymer implants (with or without cells), a collagen scaffold device made at least in part from purified natural fibers that are cross-linked to form the device and scaffolds made from synthetic polymers.

A scaffold device made from purified collagen is described in U.S. Pat. No. 6,042,610. The following U.S. Patents also disclose a meniscal augmentation device for a damaged meniscus: U.S. Pat. Nos. 5,735,903; 5,681,353; 5,306,311; 5,108,438; 5,007,934; and 4,880,429. All of these patents are incorporated by reference herein.

A scaffold device made from a synthetic polymer is described by Klompmaker, J., et al. in "Meniscal replacement using a porous polymer prosthesis: a preliminary study in the dog," Biomaterials, 17(2): pp 1169-75 (1996) and by deGroot, J. H., et al., "Use of porous polyurethanes for meniscal reconstruction and mensical prostheses," Biomaterials, 17(2): pp. 163-73 (1996). Medical applications for synthetic polymers are also disclosed in patents and patent applications, such as, for example, U.S. Pat. Nos. 6,224,892; 5,847,012 and 5,677,355.

The previous attempts at regenerating meniscal tissue have been problematic. While providing vascularity at the site of meniscal lesions may work well for more stable meniscal tears where very little tissue has been lost, providing vascularity where there is significant tissue loss (for example, due to menisectomy) has not consistently resulted in an acceptable outcome. See Arnoczky, S. P. and R. F. Warren, "The microvasculature of the meniscus and its response to injury. An experimental study in the dog, Am J Sports Med, 11(3): p.131-41 (1983); Fox, J. M., K. G. Rintz. and R. D. Ferkel, "Trephination of incomplete meniscal tears," Arthroscopy, 9(4): p. 451-5 (1993). Although autologous fibrin clot can be effective in regenerating critical sized defects, Arnoczky, S. P., R. F. Warrren, and J. M. Spivak, "Meniscal repair using an exogenous fibrin clot. An experimental study in dogs," J Bone Joint Surg Am, 70(8): pp1209-17 (1988). The fragility of a fibrin clot presents clinical challenges in handling and securing the fibrin clot to the meniscal body to obtain a sufficiently long time-of-residence. Rode, S. A., "Arthroscopic meniscal repair with use of the outside-in technique," Instr Course Lect, 49, pp 195-206 (2000).

With meniscal allografts, there is a risk of disease transfer, poor revascularization, and infiltration and breaking down by host cells resulting in joint instability. In addition, the new tissue replacing the allograft may not be of sufficient quality to restore normal function. See: Sweigart, M. A. and K. A. Athanasiou, "Toward tissue engineering of the knee meniscus," Tissue Eng., 7(2) pp 111-29 (2001); Boss, A., J. Klimkiewicz and F. H. Fu, "Technical innovation: creation of a peripheral vascularized trough to enhance healing in cryopreserved meniscal allograft reconstruction," Knee Surg Sports Traumatol Arthrosc, 8(3): pp 159-62 (2000); Siegel, M. G. and C. S. Roberts, "Meniscal allografts," Clin Sports Med," 1291: pp 59-80 (1993).

Other meniscal implants may be difficult to handle during surgery and fixation or have insufficient mechanical properties for a sufficient time-of-residence in vivo.

It is also known to use naturally occurring extracelluar matrices (ECMs) to provide a scaffold for tissue repair and regeneration. One such ECM is small intestine submucosa (SIS). SIS has been described as a natural biomaterial used to repair, support, and stabilize a wide variety of anatomical defects and traumatic injuries. The SIS material is derived from porcine small intestinal submucosa that models the qualities of its host when implanted in human soft tissues. Further, it is taught that the SIS material provides a natural matrix with a three-dimensional structure and biochemical composition that attracts host cells and supports tissue remodeling. SIS products, such as OASIS.™ and SURGISIS.™, are commercially available from Cook Biotech Inc., Bloomington, Ind.

Another SIS product, RESTORE.® Orthobiologic Implant, is available from DePuy Orthopaedics, Inc. in Warsaw, Ind. The DePuy product is described for use during rotator cuff surgery, and is provided as a resorbable framework that allows the rotator cuff tendon to regenerate. The RESTORE Implant is derived from porcine small intestine submucosa, a naturally occurring ECM composed primarily of collagenous proteins, that has been cleaned, disinfected, and sterilized. Other biological molecules, such as growth factors, glycosaminoglycans, etc., have also been identified in SIS. See: Hodde et al., Tissue Eng., 2(3): 209-217 (1996); Voytik-Harbin et al., J. Cell. Biochem., 67: 478-491 (1997); McPherson and Badylak, Tissue Eng., 4(1): 75-83 (1998); Hodde et al., Endothelium 8(1): 11-24; Hodde and Hiles, Wounds, 13(5): 195-201 (2001); Hurst and Bonner, J. Biomater. Sci. Polym. Ed., 12(11): 1267-1279 (2001); Hodde et al., Biomaterial, 23(8): 1841-1848 (2002); and Hodde, Tissue Eng., 8(2): 295-308 (2002). During nine years of preclinical testing in animals, there were no incidences of infection transmission from the implant to the host, and the RESTORE.® Orthobiologic Implant has not adversely affected the systemic activity of the immune system. See: Allman et al., Transplant, 17(11): 1631-1640 (2001); Allman et al., Tissue Eng., 8(1):53-62 (2002).

While small intestine submucosa is available, other sources of submucosa are known to be effective for tissue remodeling. These sources include, but are not limited to, stomach, bladder, alimentary, respiratory, and genital submucosa. In addition, liver basement membrane is known to be effective for tissue remodeling. See, e.g., U.S. Pat. Nos. 6,379,710, 6,171,344, 6,099,567, and 5,554,389, hereby incorporated by reference. Further, while ECM is most often porcine derived, it is known that these various ECM materials can be derived from non-porcine sources, including bovine and ovine sources. Additionally, the ECM material may also include partial layers of the lamina propria, muscularis mucosa, stratum compactum, submucosal plexuses, and vascular submucosa and/or other tissue materials depending upon factors such as the source from which the ECM material was derived and the delamination procedure.

The following patents, hereby incorporated by reference, disclose the use of ECMs for the regeneration and repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,733,337; 5,762,966; 5,755,791; 5,753,267; 5,711,969; 5,645,860; 5,641,518; 5,554,389; 5,516,533; 5,460,962; 5,445,833; 5,372,821; 5,352,463; 5,281,422; and 5,275,826.

SUMMARY OF THE INVENTION

In one aspect, the present invention provides an implantable tissue repair device comprising a cover and tissue regeneration material. The cover includes a top panel and a bottom panel joined together along a leading edge. The tissue regeneration material is positioned between the top and bottom panels. The cover includes a continuous sheet of biocompatible material extending across the edge and into the top panel and bottom panel. The cover is thicker along the leading edge than at least a portion of the top panel and thicker than at least a portion of the bottom panel. At least a portion of one of the panels covering the tissue regeneration material is thicker than a portion of the other panel covering the tissue regeneration material.

In another aspect, the present invention provides an implantable tissue repair device comprising a cover and tissue regeneration material. The cover includes a top panel and a bottom panel joined together along a leading edge. The cover includes a plurality of laminae of biocompatible material. Some of the laminae of the cover extend across the leading edge and into the top panel and bottom panel. The cover has more laminae along the leading edge than at least a portion of the top panel and has more laminae along the leading edge than at least a portion of the bottom panel; and at least a portion of one of the panels covering the tissue regeneration material has more laminae than a portion of the other panel.

In another aspect, the present invention provides an implantable tissue repair device comprising a cover and tissue regeneration material. The cover includes a top panel and a bottom panel joined together along a leading edge. The tissue regeneration material is positioned between the top and bottom panels. The tissue regeneration material has a first side and a second side. The cover includes an outer group of laminae of biocompatible material and an inner group of laminae of biocompatible material. The laminae of the inner group extend over the first side of the tissue regeneration material. The laminae of the outer group extend across the leading edge, over the laminae of the inner group and over the second side of the tissue regeneration material.

In another aspect, the present invention provides a method of making an implantable tissue repair device. The method comprises providing a mold having a cavity, a surface surrounding the cavity and a groove spaced from the cavity. A first sheet of biocompatible material is placed on the surface of the mold with part of the sheet filling the cavity and part of the sheet received in the groove. Tissue regeneration material is then placed on the portion of the first sheet in the cavity. The first sheet is then folded along the portion in the groove to cover the tissue regeneration material with the sheet.

A method of making an implantable tissue repair device includes providing a mold having a cavity and a surface surrounding the cavity. A first sheet of biocompatible material is placed on the surface of the mold. Part of the sheet is received in the cavity. Tissue regeneration material is placed on the portion of the first sheet in the cavity. A second sheet of biocompatible material is placed over the tissue regeneration material. The first sheet is then folded over the second sheet.

BRIEF DESCRIPTION OF THE DRAWINGS

The invention will be better understood by reference to the figures of the drawings wherein like reference numbers denote like parts throughout and wherein:

FIG. 1 is a perspective view of a tissue repair device or implant incorporating the principles of the present invention, showing the top surface of the implant;

FIG. 2 is a perspective view of the tissue repair device or implant of FIG. 1 showing the bottom surface of the implant;

FIG. 3 is a top plan view of the tissue repair device or implant of FIGS. 1-2;

FIG. 4 is a bottom plan view of the tissue repair device or implant of FIGS. 1-3;

FIG. 5 is a side view of the tissue repair device or implant of FIGS. 1-4;

FIG. 6 is a top plan view of one type of tissue regeneration material that may be used in the tissue repair device or implant of the present invention;

FIG. 7 is a side view of the tissue regeneration material of FIG. 6;

FIG. 8 is a diagrammatic representation of the tissue repair device or implant of FIGS. 1-5, with the wings removed and the device implanted at a defect site in a meniscus;

FIG. 8A is a diagrammatic representation of the tissue repair device or implant of FIGS. 1-5, implanted at a defect site near the posterior horn of the meniscus, with one of the wings of the device removed and the other wing secured to the patient's tibia;

FIG. 9 is an enlarged cross-sectional view of the tissue repair device or implant of FIGS. 1-5, taken along line 9-9 of FIG. 3;

FIG. 13 is an enlarged cross-section of a portion of the mold of FIGS. 10-12, showing one stage of the manufacturing process;

FIG. 14 is an enlarged cross-section of a portion of the mold of FIGS. 10-12, showing a later stage of the manufacturing process;

FIG. 15 is an enlarged cross-section of a portion of the mold of FIGS. 10-12 showing a later stage of the manufacturing process; and FIG. 16 is an enlarged cross-section of a portion of the mold of FIGS. 10-12 showing a later stage of the manufacturing process.

DETAILED DESCRIPTION OF THE ILLUSTRATED EMBODIMENT

Figure 10:
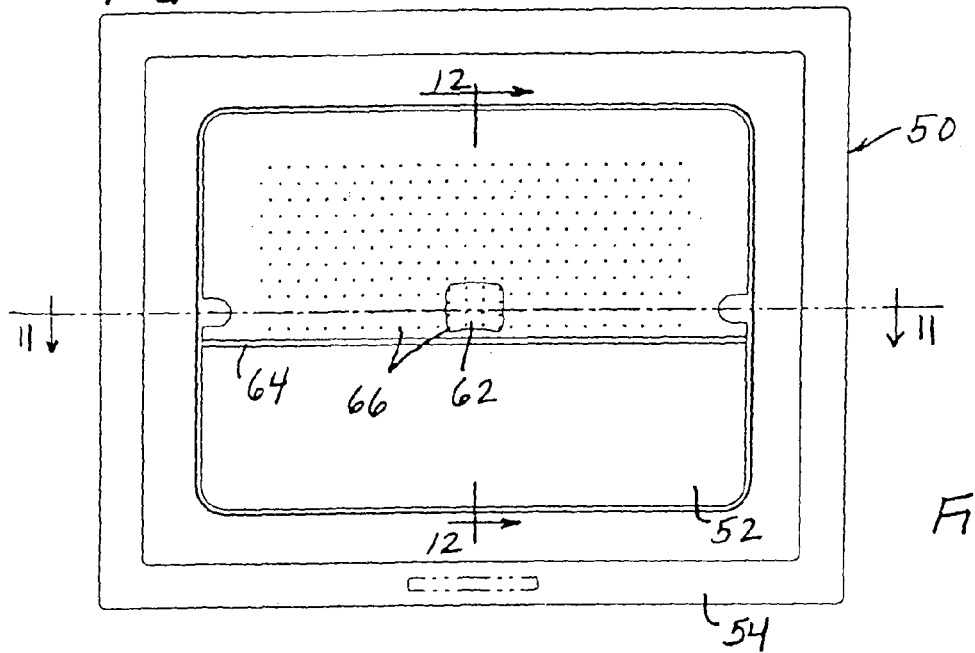
FIG. 10 is a top plan view of an apparatus for making the tissue repair device or implant of FIGS. 1-5 and 9.

An implantable tissue repair device or implant incorporating the principles of the present invention is illustrated in FIGS. 1-5, 8-9 and 16. The illustrated tissue repair device or implant 10 is a cartilage repair device, and more particularly, a meniscal repair device. However, it should be understood that the principles of the present invention may be applied to other repair devices, such as those designed to be implanted to repair defects in fibrocartilage other than the meniscus.

As shown in FIG. 9, the illustrated tissue repair device or implant 10 comprises a cover 12 and a mass of tissue regeneration material 14. In the illustrated tissue repair device or implant 10, the mass of tissue regeneration material 14 is enclosed within the cover 12. The illustrated mass of tissue regeneration material 14 is wedge shaped, with an apex 15. It should be understood that the present invention is not limited to such a wedge-shaped device unless expressly called for in the claims. The shape of the space where the implant will be implanted primarily dictates the shape of the implant. For example, if the defect space has a circular shape with a certain depth, the principles of the present invention can be used to make an implant appropriate for that application.

As shown in FIGS. 1-5 and 9, the cover 12 comprises a top portion or panel 16, a bottom portion or panel 18, and three side portions 20, 22, 24. All of the portions 16, 18, 20, 22, 24 are integral in the illustrated embodiment. The cover 12 also has a fold line 26 along its leading edge, substantially at the apex 15 of the wedge of tissue regeneration material 14. As shown in FIGS. 5 and 9, the cover is substantially flat along the leading edge 26, and the top panel 16 is parallel to the bottom panel 18. At the tissue regeneration material 14, the top panel 16 diverges from the bottom panel 18 at an angle α shown in FIG. 5. In the illustrated embodiment, the angle α is about 30°, but it should be understood that the invention is not limited to any particular angular relationship between the panels unless expressly called for in the claims.

In the illustrated embodiment, the tissue repair device 10 also includes a pair of outwardly-extending tabs or wings 23, 25. These tabs or wings 23, 25 comprise integral extensions of the cover 12, and are provided for anchoring the tissue repair device 10 to native tissue such as native parts of the meniscus. FIG. 8 illustrates a tissue repair device of the present invention implanted in a meniscus 28, shown with sutures 30 affixing the device 10 to the native meniscus 28.

The cover 12 in the illustrated embodiment comprises a plurality of sheets of bioremodelable material affixed together. Generally, as shown in FIG. 9, there are two groups of sheet laminae: an outer group of laminae 32 and an inner group of laminae 34. The outer group of laminae 32 extend along the entire length of the top portion or panel 16, across the fold line 26 and along the entire length of the bottom portion or panel 18 of the cover 12. The outer group of laminae 32 also extend across the width of the cover 12. The inner group of laminae 34 extend only along the length and width of the top portion or panel 16 of the cover 12 to the fold line 26. As shown in FIG. 9, the inner group of laminae 34 are doubled over at the fold line 26 in the illustrated embodiment. However, it should be understood that some or all of the inner group of laminae 34 need not be doubled over, and could have edges underlying the outer laminae 32 at or near the leading edge 26 of the implant 10.

Thus, the outer group of laminae 32 cover the mass of tissue regeneration material 14. The top surface 36 of the mass of tissue regeneration material 14 is covered by the doubled-over inner group of laminae 34 and the outer group of laminae 32. The leading edge 26 of the implant comprises the doubled-over inner group of laminae 34 covered by the outer group of laminae 32. The part of the top portion or panel 16 overlying the top surface 36 of the mass of tissue regeneration material 14 is three times as thick as the part of the bottom portion or panel 18 covering the remainder of the mass of tissue regeneration material. The leading edge 26 and the trailing edge 38 of the implant 10 is four times as thick as the part of the bottom portion or panel 18 covering the mass of tissue regeneration material 14. The leading edge 26 presents no exposed edges of the individual laminae, while the edges of the laminae are exposed at the trailing edge 38 of the implant 10.

In the illustrated embodiment, the outer group of laminae 32 and inner group of laminae each comprises five layers of continuous sheets of biocompatible, bioremodelable material. Thus, the leading edge 26 and trailing edge each comprise twenty layers of continuous sheets of biocompatible, bioremodelable material. The part of the top portion or panel 16 overlying the mass of tissue regeneration material 14 comprises fifteen layers of continuous biocompatible, bioremodelable material. The part of the bottom portion or panel 18 covering the remainder of the mass of tissue regeneration material 14 comprises five layers of biocompatible, bioremodelable material. It should be understood that these numbers of layers are provided as examples only; fewer or more layers could be used for either the outer group of laminae 32 or the inner group of laminae 34. Individual layers are indicated at 32A-32E and 34A-34E in FIG. 9. It should be understood that for clarity of illustration, FIG. 9 illustrates the individual layers on only portions of the cover.

In the illustrated embodiment, each layer 32A-32E and 34A-34E comprises a sheets of small intestine submucosa (SIS). Each layer forming the outer group of laminae 32 and inner group of laminae 34 could also or alternatively comprise a biocompatible polymer, or a bioremodelable collageneous tissue matrix, such as another naturally occurring extracellular matrix material, all as defined below. Each group of laminae 32, 34 could comprise a homogeneous laminate, or could comprise layers of different materials. For example, a hybrid structure like that disclosed in U.S. patent application Ser. No. 10/172,347 entitled "Hybrid Biologic-Synthetic Bioabsorbable Scaffolds", which is incorporated by reference herein in its entirety, could be used. The groups of laminae 32, 34 could comprise such materials alone or together with bioactive agents, biologically derived agents, cells, a biological lubricant or a biocompatible inorganic material, as defined below.

"Biocompatible polymers" is intended to include both synthetic polymers and biopolymers (e.g., collagen). Examples of biocompatible polymers include: polyesters of [alpha]-hydroxycarboxylic acids, such as poly(L-lactide) (PLLA), polyglycolide (PGA), self-reinforced PLLA and self-reinforced PGA; poly-p-dioxanone (abbreviated as PDO or PDS); polyhydroxyacids, poly(ortho esters); poly(beta-hydroxybutyrate) (PHB); poly (PHB-hydroxyvaleric acid), pseudo-poly(aminoacids) or polyiminocarbonates; poly(glycolide-co-trimethylene carbonate); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, copolymer or mixture of polymers or co-polymers that are utilized in the construction of prosthetic implants (e.g. 85:15 PLLA:PGA, 90:10 PGA:PLLA, or any polymer or co-polymer listed above in combination with a non-degradable material, or any combination of the above at any co-polymer ratio.) In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Bioremodelable collageneous tissue matrix" is intended to include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

"Naturally-occurring extracellular matrix material(s)" or "ECM" refers to collagen scaffolds for tissue repair and regeneration that have been derived from vertebrate tissue. One such ECM material that may be used for cartilage regeneration is submucosa, and small intestine submucosa (SIS) in particular. As used herein, "SIS" is intended to include small intestine submucosa unless otherwise limited. Moreover, as used herein, "ECM" is intended to include all SIS, as well as materials made from the other sources of submucosa (e.g. bladder, stomach and liver tissue from bovine, ovine and porcine sources) and materials derived from liver basement membrane (from whatever source) unless otherwise limited. For the purposes of this invention, it is within the definition of a naturally occurring ECM to clean, delaminate, and/or comminute the ECM, to cross-link the collagen within the ECM, and to form a foam or other structure from the ECM. It is also within the definition of naturally occurring ECM to fully or partially remove one or more components or subcomponents of the naturally occurring matrix. However, it is not within the definition of a naturally occurring ECM to extract or separate and purify the natural components or subcomponents (e.g. collagen or growth factor) and reform a matrix material from these extracted and purified components or subcomponents. Also, while reference is made to SIS, it is understood that other naturally occurring ECMs such as stomach, bladder, alimentary, respiratory, and genital submucosa, and liver basement membrane, for example, whatever the source (e.g. bovine, porcine, ovine, etc.) are within the scope of this invention. Thus, in this application, the terms "naturally occurring extracellular matrix" or "naturally occurring ECM" are intended to refer to extracellular matrix material that has been cleaned, disinfected, sterilized, and optionally cross-linked.

"Bioactive agents" include one or more of the following: chemotactic agents; therapeutic agents (e.g., antibiotics, antimicrobials, steroidal and non-steroidal analgesics and anti-inflammatories, anti-rejection agents such as immunosuppressants and anti-cancer drugs); various proteins (e.g., short chain peptides, active or inactive peptides, bone morphogenic proteins, glycoproteins and lipoproteins); cell attachment mediators; biologically active ligands; integrin binding sequence; ligands; various growth and/or differentiation agents (e.g., epidermal growth factor, IGF-I, IGF-II, TGF-β I-III, growth and differentiation factors, vascular endothelial growth factors, fibroblast growth factors, platelet derived growth factors, insulin-like growth factor and transforming growth factors, parathyroid hormone, parathyroid hormone related peptide, bFGF; TGF$_\beta$superfamily factors; bone morphogenetic proteins; BMP-2; BMP-4; BMP-6; BMP-12; sonic hedgehog; GDF5 (also known as BMP-14 or MP-52 or CDMP-1); GDF6; GDF8; CDMP-2; CDMP-3; PDGF); small molecules or protein equivalents that affect the upregulation of specific growth factors or other processes occurring during a healing response (e.g. TP508 and Chrysalin® both available from OrthoLogic, Tempe, Ariz.); tenascin-C; hyaluronic acid; chondroitin sulfate; fibronectin; decorin; thromboelastin; thrombin-derived peptides; heparin-binding domains; heparin; heparan sulfate; DNA fragments and DNA plasmids as sole constituents or when incorporated into appropriate vectors, such as viral constructs. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin (autograft, allograft and xenograft); platelet rich plasma (PRP), platelet poor plasma, bone marrow aspirate, demineralized bone matrix, insulin-like-growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically-derived agent" and "biologically-derived agents" unless expressly limited otherwise. It should be understood that the above agents are identified by way of example only, and the present invention is not limited to any particular agent unless expressly called for in the claims.

"Cells" include one or more of the following: any connective tissue cells; chondrocytes; fibrochondrocytes or any cells from fibrocartilage tissues such as meniscus and intervertebral disks (specifically the annulus fibrosus); osteocytes; osteoblasts; osteoclasts; synoviocytes; fibroblasts (including fibroblasts originating from ligaments, tendons, skin, or other tissues); bone marrow cells; mesenchymal cells; stromal cells; stem cells; embryonic stem cells; precursor cells derived from adipose tissue; peripheral blood progenitor cells; stem cells isolated from adult, adolescent, neo-natal, or fetal tissues; genetically transformed cells; a combination of any connective tissue cell type and other cells; a combination of chondrocytes and other cells; a combination of fibrochondrocytes and other cells; a combination of osteocytes and other cells; a combination of synoviocytes and other cells; a combination of fibroblasts and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult, adolescent, neo-natal, or fetal tissues and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyruvate, fungicides, antibiotics, etc., in concentrations deemed appropriate for cell type, shipping conditions, etc.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including as mucinous glycoproteins (e.g. lubricin), vitronectin, tribonectins, articular cartilage superficial zone proteins, surface-active phospholipids, lubricating glycoproteins I, II; and rooster comb hyaluronate. "Biological lubricant" is also intended to include commercial products such as ARTHREASE™ high molecular weight sodium hyaluronate, manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for opthalmologic uses). If other such substances have therapeutic value in the orthopaedic field, it is anticipated that at least some of these substances will have use in the concepts of the present disclosure, and such substances should be included in the meaning of "biological lubricant" and "biological lubricants" unless expressly limited otherwise.

"Biocompatible inorganic material(s)" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, ceramic particles, and combinations of such materials. If other such substances have therapeutic value in the orthopaedic field, it is anticipated that at least some of these substances will have use in the concepts of the present disclosure, and such substances should be included in the meaning of "biocompatible inorganic material" and "biocompatible inorganic materials" unless expressly limited otherwise.

The cover 12 of the implant 10 may be hardened or toughened as disclosed in the following United States Patent Applications which are incorporated by reference herein in their entireties: Ser. No. 10/195,719 entitled "Devices From Naturally Occurring Biologically Derived Materials" and Ser. No. 10/195,794, entitled "Meniscus Regeneration Device and Method".

The cover 12 of the implant 10 could also include fixating members such as: a length of bioresorbable suture; a bioresorbable barbed dart; a bioresorbable tack; a bioresorbable backstop; or a bioresorbable locking member, as described in U.S. patent application Ser. No. 10/195,344 entitled "Unitary Surgical Device and Method", (now U.S. Pat. No. 7,163,563) which is incorporated by reference herein in its entirety. The mass of tissue regeneration material 14 is illustrated in FIGS. 6 and 7. In the illustrated embodiment, the mass of tissue regeneration material 14 is wedge shaped, although it should be understood that other shapes are within the scope of the invention. For example, as disclosed in U.S. patent application Ser. No. 10/195,794, the mass of tissue regeneration material could comprise rolls of comminuted SIS.

The mass of tissue regeneration material 14 is illustrated in FIGS. 6 and 7. In the illustrated embodiment, the mass of tissue regeneration material 14 is wedge shaped, although it should be understood that other shapes are within the scope of the invention. For example, as disclosed in U.S. patent application Ser. No. 10/195,794, the mass of tissue regeneration material could comprise rolls of comminuted SIS.

In the illustrated embodiment, the mass of tissue regeneration material 14 comprises comminuted SIS material or SIS foam, as described in U.S. patent application Ser. No. 10/195,354 entitled "Porous Extracellular Matrix Scaffold and Method", filed by Malaviya et al., which is incorporated by reference herein in its entirety. The mass or plug of tissue regeneration material 14 may also or alternatively comprise comminuted and/or lyophilized naturally occurring ECM (e.g., SIS) with the desired porosity and material density. The material density and/or porosity of the mass or plug may be varied to control cell migration and proliferation. Additional examples of materials that are usable for the mass of tissue regeneration material include ECM (e.g., SIS) powder, ECM (e.g., SIS) fibers, ECM (e.g., SIS) threads, ECM (e.g., SIS) mesh, ECM (e.g., SIS) wovens, ECM (e.g., SIS) non-wovens, ECM (e.g., SIS) braided materials, ECM (e.g., SIS) solutions, ECM (e.g., SIS) gel, ECM (e.g., SIS) paste, ECM (e.g., SIS) foam, and combinations of such materials. For the powder, solutions, gel and paste forms of SIS, the material may be prepared as described in U.S. Pat. No. 5,352,463, entitled "Tissue Graft for Surgical Reconstruction of a Collagenous Meniscus and Method Therefor", which is incorporated by reference herein in its entirety. In addition, unless expressly limited by the claims, the mass of tissue regeneration material could also comprise bioremodelable collageneous tissue matrices, either alone or in combination with an ECM. Moreover, the mass of tissue regeneration material could comprise a hybrid of a biocompatible polymer with and ECM or bioremodelable collageneous tissue matrix, as disclosed in U.S. patent application Ser. Nos. 10/195,341, entitled "Hybrid Biologics/Synthetic Porous Extracellular Matrix Scaffolds" and 10/172,347 entitled "Hybrid Biologic-Synthetic Bioabsorbable Scaffolds", which are incorporated by reference herein in their entireties. It should be understood that separate reference in the above list to the forms of ECM should not be taken to imply that the listed references are exclusive; for example, ECM non-wovens, ECM threads and ECM foam may all include ECM fibers.

The mass of tissue regeneration material 14 may also include bioactive agents, biologically derived agents, cells, a biological lubricant or a biocompatible inorganic material, as defined above.

Figure 12:
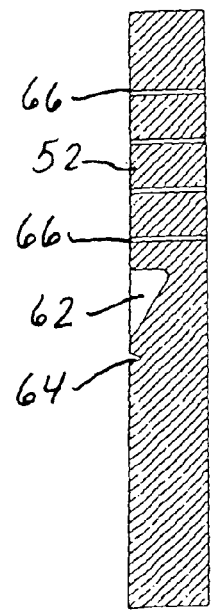
FIG. 12 is a cross-section of the mold of FIGS. 10-11, taken along line 12-12 of FIG. 10.
Figure 11:
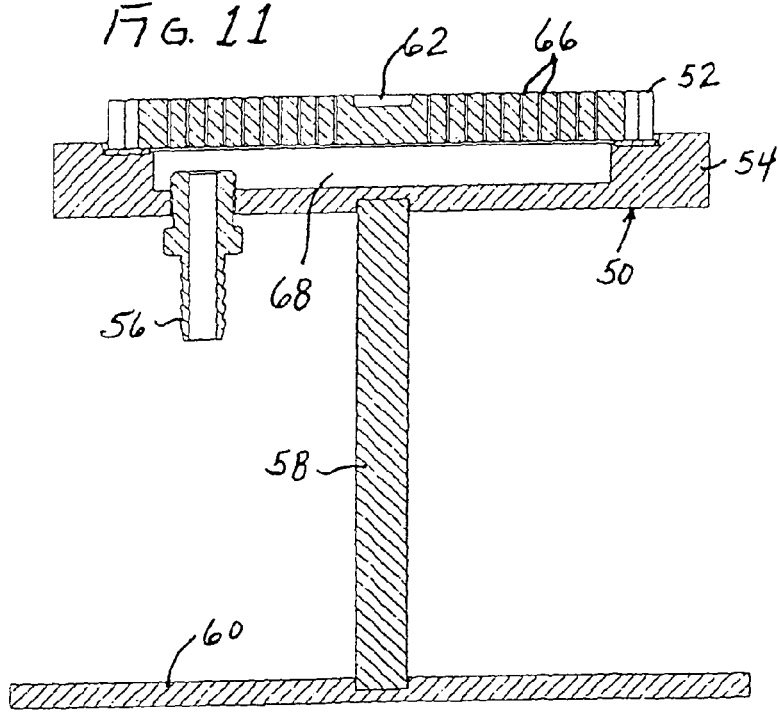
FIG. 11 is a cross-section of the device taken along line 11-11 of FIG. 10.

An apparatus 50 for making the illustrated tissue repair device or implant 10 is shown in FIGS. 10-12. The apparatus 50 comprises a mold 52, a vacuum fixture 54, a nipple fitting 56, a fixture post 58 and a fixture base 60. The mold 52 includes a cavity 62, an elongate groove 64 spaced from the cavity 62 and a plurality of air vents 66 across the surface of the mold. The air vents 66 extend through the thickness of the mold and communicate with a plenum 68 in the vacuum fixture 54. The nipple fitting 56 also communicates with the plenum 68. A suitable hose (not shown) and vacuum pump (not shown) are connected to the nipple fitting 56 to draw air through the air vents 66, into the plenum 68 and out through the nipple fitting 56.

The mold cavity 62 is shaped to correspond generally with the shape of the mass of tissue regeneration material 14. As described in more detail below, the mold groove 64 is used to define the fold line or leading edge 26 of the implant 10.

The steps of making the implant 10 are illustrated in FIGS. 13-16. First, individual layers of thin, moist, flexible sheets of the cover material, such as SIS, are laid out on top of each other and partially laminated by hand pressure to form the outer group of laminae 32 into an outer laminate sheet. In the illustrated embodiment, five thin sheets of SIS are layered together to form the outer group 32 of laminae into the outer laminate sheet. This outer laminate sheet (that is, the outer group 32 of laminae) is then laid on the top surface of the mold 52. The outer laminate sheet comprising has an area generally great enough to cover the entire top surface of the mold 52. The vacuum pulls the outer laminate sheet against the surface of the mold and into the cavity 62. Part of the outer laminate sheet also lays in the groove 64. At the end of this step in the manufacturing process, the outer laminate sheet generally conforms to the shape of the top surface of the mold 52, as shown in FIG. 13.

Next, the mass of tissue regeneration material 14 is placed in the cavity 62 that is lined by the outer laminate, as shown in FIG. 14. The mass of tissue regeneration material can be pre-shaped or could comprise loose particles.

Next, individual layers of moist, flexible sheets of the cover material, such as SIS, are laid out on top of each other and partially laminated by hand pressure to form the inner group of laminae 34 into an inner laminate sheet. In the illustrated embodiment, five thin sheets of SIS are layered together to form the inner laminate sheet (that is, the inner group of laminae 34). This inner laminate sheet is then laid on top of the outer laminate sheet and the mass of tissue regeneration material 14 as shown in FIG. 15. The inner laminate sheet has an area generally great enough to cover the entire surface of the outer laminate sheet and the mass of tissue regeneration material 14. As the inner laminate sheet is laid flat on the mold 52, the vacuum pulls the inner laminate sheet against the surfaces of the outer laminate sheet and the mass of tissue regeneration material. Part of the inner laminate sheet lays in the groove 64 as well.

Next, the outer laminate sheet and inner laminate sheet are folded along the portions received in the groove 64, back over the mass of tissue regeneration material 14. As shown in FIG. 16, the result is a structure having the greatest number of layers or laminae of the cover material at the leading and trailing edges 26, 38.

The raw implant may then be high pressure laminated while in the mold 52 and dried while still in the mold 52 in a vacuum drying bed. This drying step may still leave the mass of tissue regeneration material in a wet state. The semi-finished implant may then be lyophilized to dry the mass of tissue regeneration material. Finally, the cover may be trimmed to form the implant as shown in FIGS. 1-4. It is expected that standard disinfection and sterilization techniques may be used with the implants produced by this method.

It should be understood that the above-described method of making the implant is provided as an example only. The invention is not limited to any particular method unless expressly called for in the claims.

It is anticipated that several different sizes and shapes of implants 10 would be made available to account for differences in the amount of tissue removed in a menisectomy. Accordingly, there would also be several different molds provided to produce these different sizes of implants 10.

Accordingly, there would also be several different cutting dyes provided to produce these different implants.

It should be understood that the above-described manufacturing process is provided as an example only. The present invention is not limited to this process unless expressly set forth in the claims.

To use the implant of the present invention, the surgeon would perform a partial menisectomy to remove diseased or damaged meniscal tissue. The implant 10 would be hydrated and then delivered to the site of the defect and fixated to the native meniscal tissue using suture or other fixating mechanisms. To deliver the implant 10 arthroscopically, devices may be used; like those disclosed in the following United States patent applications, which are incorporated by reference herein in their entireties: U.S. patent application Ser. No. 10/610,287 entitled Slide and Kit for Delivering Orthopaedic Implants (filed Jun. 30, 2003) and U.S. Provisional Patent Application Serial No. 60/483,804 entitled Instrument for Delivery of Implant (filed Jun. 30, 2003). However, the present invention is not limited to any particular surgical technique or surgical instrument unless expressly set forth in the claims.

If there is sufficient native meniscal tissue present, the wings 23, 25 may be cut off the implant 10 and the implant fixated as shown in FIG. 8. If insufficient native meniscal tissue is present, such as if the implant 10 is to be affixed near the posterior horn of the meniscus 28, one of the wings 23, 25 may be cut off and the other left. As shown in FIG. 8A, the surgeon can then use the remaining wing (25 in FIG. 8A) to fix the implant directly to the patient's tibia 70, for example by inserting a screw 72 through the wing 25 and into the tibia 70.

Use of the implant of the present invention may be accompanied by use of a biological lubricant, as disclosed in U.S. patent application Ser. No. 10/195,606 entitled "Cartilage Repair and Regeneration Device and Method" and 10/195,334 entitled "Cartilage Repair and Regeneration Scaffold and Method", incorporated by reference herein in their entireties.

A tissue repair device or implant 10 made according to the above described process was tested as follows. The device was implanted in a meniscal defect of a goat knee. The goat knee and implant were placed in a test apparatus with the knee joint at about 135° of flexion. Axial compression of 70+/−30 pounds was applied as the knee was moved through 5° of flexion/extension and as the tibia was translated +/−⅛ inch in the anterior/posterior direction. The test was conducted for 100,000 cycles at 2 Hz, with an intermittent phosphate buffered saline (PBS, pH 7.2) mist. At the end of the test, the implant lost only 6.9+/−1.3% of its dry weight. There were no incidences of the implant delaminating at the leading edge 26; the only delamination that occurred was at the periphery of the implant. However, the implant did not fail because it was held together at the site of delamination by sutures.

Thus, the implant of the present invention is mechanically robust and should be capable of withstanding handling and hydration during implantation without undergoing delamination.

While only a specific embodiment of the invention has been shown, it is apparent that various alternatives and modifications can be made thereto. For example, the shape of the implant could be modified for use in replacing resected tissue from other joints, such as intra-articular cartilage in the temporomandibular joint or between vertebrae, for example. Moreover, those skilled in the art will also recognize that certain additions can be made to the illustrated embodiment. It is, therefore, the intention in the appended claims to cover all such alternatives, modifications and additions as may fall within the true scope of the invention.

The invention claimed is:

1. An implantable tissue repair device comprising:
   a cover including a top panel and a bottom panel joined together along a leading edge;
   tissue regeneration material between the top and bottom panels;
   wherein:
   the cover includes a plurality of laminae of biocompatible material;
   some of the laminae of the cover extend across the leading edge and into the top panel and bottom panel;
   the cover has more laminae along the leading edge than at least a portion of the top panel and has more laminae along the leading edge than at least a portion of the bottom panel;
   at least a portion of one of the panels covering the tissue regeneration material has more laminae than a portion of the other panel; and
   at least one of the cover and the tissue regeneration material includes a material selected from the group consisting of:
   small intestine submucosa,
   stomach submucosa,
   bladder submucosa,
   alimentary submucosa,
   respiratory submucosa,
   genital submucosa, and
   liver basement membrane.

2. The implantable tissue repair device of claim 1 wherein at least part of the top panel is parallel to at least part of the bottom panel along at least part of the leading edge.

3. The implantable tissue repair device of claim 1 wherein the top panel and bottom panel are joined together along a trailing edge.

4. The implantable tissue repair device of claim 1 wherein the laminae comprise sheets of small intestine submucosa.

5. The implantable tissue repair device of claim 4 wherein the tissue regeneration material includes small intestine submucosa.

6. The implantable tissue repair device of claim 1 wherein the leading edge comprises a fold line.

7. The implantable tissue repair device of claim 1 wherein the device is sized and shaped to be used as a mensical implant.

8. An implantable tissue repair device comprising:
   a cover including a top panel and a bottom panel joined together along a leading edge;
   tissue regeneration material between the top and bottom panels, the tissue regeneration material having a first side and a second side meeting at an apex, the tissue regeneration material further including a third side extending between the first side and the second side;
   wherein:
   the cover includes an outer group of laminae of biocompatible material and an inner group of laminae of biocompatible material;
   the laminae of the inner group extend over the first side of the tissue regeneration material;
   the laminae of the outer group extend across the leading edge, over the laminae of the inner group and over the second side and third side of the tissue regeneration material;
   the cover is thicker over the first side of the tissue regeneration material than over the second side and third side of the tissue regeneration material; and at least one of the cover and the tissue regeneration material includes a material selected from the group consisting of:
small intestine submucosa,
stomach submucosa,
bladder submucosa,
alimentary submucosa,
respiratory submucosa,
genital submucosa, and
liver basement membrane.

9. The implantable tissue repair device of claim 8 wherein at least part of the top panel is parallel to at least part of the bottom panel along at least part of the leading edge.

10. The implantable tissue repair device of claim 8 wherein the top panel and bottom panel are joined together along a trailing edge.

11. The implantable tissue repair device of claim 8 wherein the laminae of the outer group comprise sheets of small intestine submucosa.

12. The implantable tissue repair device of claim 11 wherein the laminae of the inner group comprise sheets of small intestine submucosa.

13. The implantable tissue repair device of claim 8 wherein the tissue regeneration material includes small intestine submucosa.

14. The implantable tissue repair device of claim 8 wherein the leading edge comprises a fold line.

15. The implantable tissue repair device of claim 8 wherein the device is sized and shaped to be used as a mensical implant.

16. The implantable tissue repair device of claim 1 wherein the tissue regeneration material includes a material selected from the group consisting of:
comminuted small intestine submucosa,
comminuted stomach submucosa,
comminuted bladder submucosa,
comminuted alimentary submucosa,
comminuted respiratory submucosa,
comminuted genital submucosa, and
comminuted liver basement membrane.

17. The implantable tissue repair device of claim 16 wherein the cover includes a material selected from the group consisting of:
small intestine submucosa,
stomach submucosa,
bladder submucosa,
alimentary submucosa,
respiratory submucosa,
genital submucosa, and
liver basement membrane.

18. The implantable tissue repair device of claim 8 wherein the tissue regeneration material includes a material selected from the group consisting of:
comminuted small intestine submucosa,
comminuted stomach submucosa,
comminuted bladder submucosa,
comminuted alimentary submucosa,
comminuted respiratory submucosa,
comminuted genital submucosa, and
comminuted liver basement membrane.

19. The implantable tissue repair device of claim 18 wherein the cover includes a material selected from the group consisting of:
small intestine submucosa,
stomach submucosa,
bladder submucosa,
alimentary submucosa,
respiratory submucosa,
genital submucosa, and
liver basement membrane.

* * * * *